(12) United States Patent
Carlson

(10) Patent No.: US 12,281,355 B2
(45) Date of Patent: Apr. 22, 2025

(54) MULTIPLEXED IMAGING WITH ENZYME MEDIATED AMPLIFICATION

(71) Applicant: Akoya Biosciences, Inc., Menlo Park, CA (US)

(72) Inventor: Grady Carlson, Houston, TX (US)

(73) Assignee: Akoya Biosciences, Inc., Menlo Park, CA (US)

( * ) Notice: Subject to any disclaimer, the term of this patent is extended or adjusted under 35 U.S.C. 154(b) by 694 days.

(21) Appl. No.: 17/039,888

(22) Filed: Sep. 30, 2020

(65) Prior Publication Data
US 2021/0222234 A1 Jul. 22, 2021

Related U.S. Application Data

(60) Provisional application No. 62/908,540, filed on Sep. 30, 2019.

(51) Int. Cl.
*C12Q 1/6832* (2018.01)
*C12Q 1/6804* (2018.01)
*G01N 1/30* (2006.01)

(52) U.S. Cl.
CPC ......... *C12Q 1/6832* (2013.01); *C12Q 1/6804* (2013.01); *G01N 1/30* (2013.01)

(58) Field of Classification Search
CPC ...... C12Q 1/6832; C12Q 1/6804; C12Q 1/28; C12Q 1/6841; C12Q 2521/543; C12Q 2537/143; C12Q 2563/107; C12Q 2563/125; C12Q 2563/131; C12Q 2543/10; C12Q 2563/179; C12Q 2565/518; G01N 1/30; G01N 33/54306
See application file for complete search history.

(56) References Cited

U.S. PATENT DOCUMENTS

| | | |
|---|---|---|
| 5,391,723 A | 2/1995 | Priest |
| 6,372,937 B1 | 4/2002 | Bobrow et al. |
| 6,735,531 B2 | 5/2004 | Rhett et al. |
| 6,828,109 B2 | 12/2004 | Kaplan |
| 7,019,777 B2 | 3/2006 | Sun |
| 7,226,788 B2 | 6/2007 | De La Torre-Bueno |
| 7,555,155 B2 | 6/2009 | Levenson et al. |
| 7,729,125 B2 | 6/2010 | Araki et al. |
| 9,107,624 B2 | 8/2015 | Darty |
| 9,909,167 B2 | 3/2018 | Samusik et al. |
| 10,370,698 B2 | 8/2019 | Nolan et al. |
| 10,871,485 B2 | 12/2020 | Campton et al. |
| 2005/0003462 A1 | 1/2005 | Kaplan |
| 2013/0260379 A1 | 10/2013 | Alexander et al. |
| 2017/0226572 A1 | 8/2017 | Armitage et al. |
| 2018/0164308 A1 | 6/2018 | Walter et al. |
| 2020/0393343 A1 | 12/2020 | Kennedy-Darling et al. |

FOREIGN PATENT DOCUMENTS

| | | | |
|---|---|---|---|
| JP | 2018-506726 A5 | 3/2019 | |
| JP | 2021-525877 A | 9/2021 | |
| WO | WO 2005/040769 | 5/2005 | |
| WO | WO 2016/061460 | 4/2016 | ............... C12Q 1/28 |
| WO | WO 2016/127149 A2 | 8/2016 | |
| WO | WO 2019/236841 | 12/2019 | ........... C12Q 1/6804 |
| WO | WO 2020/163397 | 8/2020 | |

OTHER PUBLICATIONS

Li et al, Comparative study of some synthesised and commercial fluorogenic substrates for horseradish peroxidase and its mimetic enzyme hemin by a flow injection method, 1997, Analytica Chimica Acta 340 , 159-168 (Year: 1997).*
McEldoon et al, Unusual Thermal Stability of Soybean Peroxidase, 1996, Biotechnol. Prog., 12, 555-558 (Year: 1996).*
The International Search Report and Written Opinion of the International Searching Authority for International Application No. PCT/US2020/053600, dated Jan. 27, 2021.
Taofiq et al., "Hydroxycinnamic Acids and Their Derivatives: Cosmeceutical Significance, Challenges and Future Perspectives, a Review," Molecules, 2017, 22(2):281 (24 pages).
Glass et al., "Simple: A Sequential Immunoperoxidase Labeling and Erasing Method," J. Histochem. Cytochem., Oct. 2009, 57(10): 899-905.
Dennler et al., "Antibody Conjugates: From Heterogeneous Populations to Defined Reagents," Antibodies, Aug. 2015, 4:197-224.
Kozlov et al., "Efficient strategies for the conjugation of oligonucleotides to antibodies enabling highly sensitive protein detection," Biopolymers, Mar. 8, 2004, 73(5):621-630.
Van Gijlswijk et al., "Horseradish peroxidase-labeled oligonucleotides and fluorescent tyramides for rapid detection of chromosome-specific repeat sequences," Cytogenet. Cell Genet., 1996, 75(4):258-262.
Spicer et al., "Achieving Controlled Biomolecule-Biomaterial Conjugation," Chem. Rev., 2018, 118(16):7702-7743.
Winkler, Johannes, "Oligonucleotide conjugates for therapeutic applications," Ther. Deliv., 2013, 4(7):791- 809.

(Continued)

*Primary Examiner* — Narayan K Bhat
(74) *Attorney, Agent, or Firm* — Fish & Richardson P.C.

(57) ABSTRACT

Methods for imaging an analyte in a sample include contacting the biological sample with a binding agent, where the binding agent includes a binding moiety that binds to the analyte and a first nucleotide sequence, contacting the biological sample with a catalytic agent, where the catalytic agent includes a second nucleotide sequence linked to an enzyme, and where the second nucleotide sequence hybridizes to the first nucleotide sequence, contacting the biological sample with a localization agent, where the localization agent includes a substrate complementary to the enzyme and a third nucleotide sequence linked to the substrate, and contacting the biological sample with a labeling agent, where the labeling agent includes a fourth nucleotide sequence linked to an optical label, where the fourth nucleotide sequence hybridizes to the third nucleotide sequence.

32 Claims, 5 Drawing Sheets

(56) References Cited

OTHER PUBLICATIONS

Van Gijlswijk et al., "Synthesis and purification of horseradish peroxidase-labeled oligonucleotides for tyramide-based fluorescence in situ hybridization," Histochem. Cell Biol., 2000, 113(3):175-180.
Hwang, Gil Tae, "Single-Labeled Oligonucleotides Showing Fluorescence Changes upon Hybridization with Target Nucleic Acids," Molecules, Jan. 8, 2018, 23(1): 124 (19 pages).
Taskova et al., "Fluorescent Oligonucleotides with Bis(prop-2-yn-1-yloxy)butane-1,3-diol Scaffold Rapidly Detect Disease-Associated Nucleic Acids," Bioconjugate Chem., Dec. 2, 2019, 30(12):3007-3012.
Genfa et al., "Hematin as a Peroxidase Substitute in Hydrogen Peroxide Determinations," Anal. Chem., Mar. 1, 1992, vol. 64: 517-522.
Ikariyama et al., "Solid-Phase Luminescent Catalyst Immunoassay for Human Serum Albumin with Hemin as Labeling Catalyst," Analytica Chimica Acta, 1984, vol. 156: 245-252.
Office Action in Japanese Appln. No. 2022-520099, dated Aug. 5, 2024, 32 pages (with English translation).
Zhang, "Fully automated 5-plex fluorescent immunohistochemistry with tyramide signal amplification and same species antibodies," Laboratory Investigation, May 15, 2017, vol. 97, pp. 873-885.
Office Action in European Appln. No. 20793224.5, dated Jan. 14, 2025, 6 pages.

\* cited by examiner

MULTIPLEXED IMAGING WITH ENZYME MEDIATED AMPLIFICATION

CROSS-REFERENCE TO RELATED APPLICATIONS

This application claims priority to U.S. Provisional Patent Application No. 62/908,540, filed on Sep. 30, 2019, the entire contents of which are incorporated by reference herein.

BACKGROUND

Antibodies were first employed in tissue section analysis in 1942 to visualize pneumococcal antigens in organ biopsies from mice infused with live bacteria. Since that time, immunohistochemistry has become a mainstay of clinical diagnostics and basic research.

However, conventional immunohistochemistry (IHC) methods do not necessarily provide adequate signal for detection, particularly for immunological targets that are weakly expressed or which are not efficiently targeted by existing IHC reagents.

SUMMARY

The present disclosure features methods, compositions of matter, and kits for performing immunohistochemistry on biological samples, with tyramide signal amplification to enhance detection of targets using chromogenic or fluorescent dyes, where the dyes can be removed after detection. Multiplexed detection can be performed at high levels of multiplexing through successive rounds of imaging, where each imaging round can detect multiple dyes corresponding to multiple targets, and amplification can be used for any or all targets.

In some embodiments, the methods include enzyme-mediated deposition of oligonucleotide sequences onto a sample using the TSA methodology. Because the enzyme moiety coupled to each antibody molecule can catalyze deposition of many oligo-sequence molecules onto the sample, the methods realize amplification (i.e., a greater than 1:1 ratio of the amount of dye molecules to the amount of target molecules). This process can be repeated for multiple antibodies, providing TSA-amplified deposition of multiple oligonucleotide sequences on the sample.

One or more dyes labeled with countersense oligonucleotide sequences are introduced, and hybridize with the corresponding (i.e., complementary) TSA-deposited oligonucleotide sequences and are detected, after which the oligonucleotide-labeled dyes can be dehybridized and removed from the sample. One or more additional detection rounds can optionally be performed.

In some embodiments, a sample is incubated with multiple primary antibodies, each of which targets a different analyte of interest and localizes at sites corresponding to that target analyte in the sample. Each different type of antibody is conjugated to a unique oligonucleotide sequence $S_i$ drawn from a group of N sequences $S=\{S_1, S_2 \ldots S_N\}$, where the group S is orthogonal, meaning that a countersense sequence $S_i'$ for a given $S_i$ hybridizes under stringent conditions substantially only with $S_i$, and not with any $S_j$ where $i \neq j$. In the context of the group of sequences S, "substantially" means that the total amount of cross-binding of sequence $S_i'$ with sequences $S_j$ other than $S_i$ is less than 1% of the amount of binding of sequence $S_i'$ to sequence $S_i$.

Blocking and washing steps can be performed as is typical during immunohistochemical antibody incubation, to minimize nonspecific binding during incubation and to remove excess antibodies afterward. Fixation step a can be performed afterward to link the primary antibodies more firmly to the sample and reduce the likelihood they will be removed during subsequent steps.

An enzyme such as horseradish peroxidase (HRP) is conjugated to countersense sequence $S_i'$ and applied to the sample, where the countersense sequence $S_i'$ hybridizes with the corresponding sequence $S_i$ linked to the primary antibody by binding along at least a first binding region. Stringent or near-stringent conditions can be used to minimize cross-hybridization with other sequences and/or at other locations in the sample. Because the primary antibodies are conjugated with different sequences $S_i$ drawn from the orthogonal group S, little or no enzyme localizes at primary antibodies that specifically bind to other target analytes.

Separately, a localization agent includes an oligonucleotide sequence $S_k$ conjugated to a substrate for the HRP enzyme. In some preferred embodiments, the substrate can be a tyramine compound (i.e., a tyramine-containing compound), a compound that contains a tyramine derivative, p-hydroxy-cinnamic acid, or a derivative of p-hydroxy-cinnamic acid. Suitable derivatives of tyramine include, but are not limited to, a tyramine moiety with one or more (e.g., two or more, three or more) substituents on the amine group, such as one or more alkyl, alkenyl, alkynl, hydroxyl, halide, and/or alkoxy groups. Suitable derivatives of p-hydroxy-cinnamic acid include, but are not limited to, derivatives described in Taofiq et al., Molecules 22(2): 281 (2017), the entire contents of which are incorporated by reference.

In some embodiments, the oligonucleotide sequence is the same as that on the associated primary antibody (k=i). In other embodiments, it is a different sequence (k≠i) that is also different from the sequences conjugated to any other primary antibodies.

The oligonucleotide-labeled enzyme substrate is then applied to the sample, resulting in enzyme-catalyzed deposition of oligonucleotide molecules having sequence $S_k$ to the sample, near the target antibody, through tyramide signal amplification. A dehybridization step is performed, releasing oligonucleotide-conjugated enzymes (e.g., HRP) from its associated antibody, and the enzymes are removed by one or more washing steps.

The foregoing procedure corresponds to one round of amplified oligonucleotide deposition, resulting in some number of oligonucleotides molecules of sequence $S_k$ being covalently bound to the sample in the vicinity of each primary antibody. The average number of such molecules is the degree of amplification attained through the TSA mechanism.

Amplified deposition can be performed for multiple antibody species, resulting in deposition of oligonucleotide sequences of different $S_k$ types at sample locations corresponding to the multiple primary antibodies. The number of rounds of TSA-amplified oligo-deposition can be 1, if amplification is only sought for one target in the sample; or it can be some number M less than the number of primary antibodies N, if amplification is desired for a subset of markers; or it can be N if amplification is sought for all markers.

Detection can be performed by introducing one or more oligonucleotide-labeled dyes, each oligonucleotide having a sequence $S_k'$. Each such oligonucleotide-conjugated dye molecule hybridizes with TSA-deposited oligonucleotide sequence having the mating-sequence $S_k$ by binding along at least a first binding region. Stringent or near-stringent conditions can be imposed, along with washing steps to remove excess oligonucleotide-conjugated dye molecules, to minimize dye binding at other sites in the sample.

The sample is then imaged with a fluorescence microscope, if fluorescent dyes are used, or a brightfield microscope if chromogenic dyes are used. This constitutes one detection round. Afterwards, a dehybridization step is performed, releasing the oligo-labeled dyes, and they can be removed by one or more washing steps.

In some embodiments 2 or more dyes (e.g., 3 or more, 4 or more, 5 or more, 6 or more, 8 or more, 10 or more, or even more dyes) are imaged in each detection round, using a multi-channel fluorescence microscope to detect each dye individually. In certain embodiments, up to 6 dyes or more are imaged, using spectral imaging and unmixing techniques. In general, the number of dyes B that can be imaged in a single round depends on the capabilities of the microscope and the analysis techniques used to interpret its imagery.

A counterstain such as DAPI can be imaged once, or during each imaging cycle, and this can be used to register images of the oligonucleotide-labeled dyes from successive imaging rounds in order to form an overall multiplexed image of the sample where images from all rounds are spatially co-registered.

Accordingly, highly multiplexed images can be obtained. The overall number of targets N that can be imaged is based on the number of antibodies labeled with orthogonal oligonucleotide sequences; it is not limited to the number of dyes B that can be imaged in a single imaging round, nor by the number of rounds M of TSA-based oligonucleotide deposition.

The use of amplification via HRP-catalyzed deposition of oligonucleotides can be combined with non-amplified detection. Certain workflows can include some oligonucleotide-labeled antibodies that hybridize with oligonucleotide-labeled HRP, catalyze deposition of multiple oligonucleotides on the sample via the TSA reaction, and are detected via oligonucleotide-labeled dyes that couple with these deposited oligonucleotides, while other oligonucleotide-labeled antibodies are detected by hybridizing with oligonucleotide-labeled dyes. Thus, workflows can incorporate amplification for detection of some antibodies, and not for others.

In some embodiments, enzymes such as HRP can be localized at antibody sites by other means such as indirect labeling to deposit oligonucleotides in the sample. Primary antibodies can bind to specific target analytes in a sample as described above, and then enzymes conjugated to a binding entity such as a secondary antibody or nanobody that binds to the primary antibodies can be introduced, so that the enzymes are indirectly linked to the primary antibodies.

As one example, a primary antibody which is the E1L3N clone for PDL-1 can be incubated with the sample to localize at PDL-1 sites in a sample; a secondary antibody consisting of Leica Power Vision Poly HRP can localize at the primary antibody sites and catalyze deposition of oligonucleotides with sequence $S_k$ onto the sample adjacent the antibody locations. Stripping techniques such as elution with citrate antigen retrieval solution can be used to remove the primary and secondary antibodies, leaving the deposited oligonucleotides in place. This can be repeated with other antibodies and other selected $S_k$ to provide HRP-amplified deposition of multiple oligonucleotides corresponding to multiple targets, which can be detected using oligo-labeled dyes as previously described.

The dyes used in each labeling and imaging cycle can be the same or different, and the same number or different numbers of dyes can be used and imaged in each cycle. The goal is typically to image all targets of interest, but the specific dyes used, and the way they are grouped into rounds, can be chosen according to specific attributes of the analytes, sample, and workflow conditions. For example, one may choose to image several targets for which the density of TSA-deposited oligonucleotides is high in one imaging round, using relatively short exposure times; and to image other targets for which there are fewer TSA-deposited oligonucleotides in another imaging round, using relatively shorter exposure times. Grouping targets in a selected way can be beneficial in terms of practical factors such as exposure time, image registration, and other factors particular to certain workflows.

The biological sample can be selected from the group consisting of: biological tissue, cultured cells, and cells taken from an animal subject of interest. In some embodiments, the biological sample includes material that is human origin or mouse origin. In some embodiments, the biological sample is fresh, frozen, or fixed. In some embodiments it can be a section or core obtained from a formalin-fixed paraffin-embedded (FFPE) tissue block. The sample can include material from a tissue section, tissue micro-array (TMA), cell pellet, core biopsy, needle biopsy, or cells obtained from a blood or serum sample.

In some embodiments, the biological sample is immobilized on a surface such as a slide, a plate, a well, or a film.

In some embodiments, the primary and/or secondary antibody or antibody fragment comprises an IgG, an IgM, a monoclonal antibody, a scFv, a nanobody, a Fab, or a diabody. In some embodiments, the antibody or antibody fragment is specific for an element of the sample such as a protein, or for another antibody or antibody fragment (e.g., for indirect linking).

In some embodiments, the oligonucleotide sequence $S_i$ conjugated to the antibody comprises a plurality of ribonucleic acids. In some embodiments, it comprises a plurality of deoxyribonucleic acids. In some embodiments, the $S_i$ oligonucleotide is at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 nucleotides long. In some embodiments, the $S_i$ oligonucleotide is between 10-30, between 10-50, between 10-70, between 10-100, between 20-50, between 20-70, between 20-100, between 30-50, between 30-70, between 30-100, between 40-70, between 40-100, between 50-70, between 50-100, between 60-70, between 60-80, between 60-90, or between 60-100 nucleotides in length.

In some embodiments, the $S_i$ oligonucleotide is no more than 5, no more than 10, no more than 15, no more than 20, no more than 25, no more than 30, no more than 35, no more than 40, no more than 45, no more than 50, no more than 55, no more than 60, no more than 65, no more than 70, no more than 75, no more than 80, no more than 85, no more than 90, no more than 95, or no more than 100 nucleotides long.

In some embodiments, the $S_i$ oligonucleotide comprises one or more synthetic nucleotides. In some embodiments, the $S_i$ oligonucleotide is wholly single stranded. In some embodiments, the $S_i$ oligonucleotide is partially double stranded.

In some embodiments, the first binding region of said $S_i'$ oligonucleotide is complementary to at least a portion of said first oligonucleotide $S_i$. In some embodiments, the first binding region of the $S_i'$ oligonucleotide is at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 nucleotides long. In some embodiments, the first binding region of the $S_i'$ oligonucleotide is between 10-30, between 10-50, between 10-70, between 10-100, between 20-50, between 20-70, between 20-100, between 30-50, between 30-70, between 30-100, between 40-70, between 40-100, between 50-70, between 50-100, between 60-70, between 60-80, between 60-90, or between 60-100 nucleotides in length.

In some embodiments, the binding region of the $S_i'$ oligonucleotide is no more than 5, no more than 10, no more than 15, no more than 20, no more than 25, no more than 30, no more than 35, no more than 40, no more than 45, no more than 50, no more than 55, no more than 60, no more than 65, no more than 70, no more than 75, no more than 80, no more than 85, no more than 90, no more than 95, or no more than 100 nucleotides long.

In some embodiments, the binding region of the $S_i'$ oligonucleotide comprises one or more synthetic nucleotides. In some embodiments, the $S_i'$ oligonucleotide comprises a plurality of ribonucleic acids. In some embodiments, the $S_i'$ oligonucleotide comprises a plurality of deoxyribonucleic acids.

In some embodiments, the $S_i'$ oligonucleotide is at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 nucleotides long. In some embodiments, the second oligonucleotide is between 10-30, between 10-50, between 10-70, between 10-100, between 20-50, between 20-70, between 20-100, between 30-50, between 30-70, between 30-100, between 40-70, between 40-100, between 50-70, between 50-100, between 60-70, between 60-80, between 60-90, or between 60-100 nucleotides in length. In some embodiments, the second oligonucleotide is no more than 5, no more than 10, no more than 15, no more than 20, no more than 25, no more than 30, no more than 35, no more than 40, no more than 45, no more than 50, no more than 55, no more than 60, no more than 65, no more than 70, no more than 75, no more than 80, no more than 85, no more than 90, no more than 95, or no more than 100 nucleotides long.

In some embodiments, the $S_i'$ oligonucleotide comprises one or more synthetic nucleotides. In some embodiments, the $S_i'$ oligonucleotide is wholly single stranded. In some embodiments, the $S_i'$ oligonucleotide is partially double stranded.

In some embodiments, the enzyme is horseradish peroxidase (HRP). In some embodiments, the enzyme can be a hemin-containing complex which can mimic HRP, such as hematin. In some embodiments, the enzyme can be soybean peroxidase.

In some embodiments, the oligonucleotide sequence $S_k$ conjugated to the substrate material comprises a plurality of ribonucleic acids. In some embodiments, $S_k$ comprises a plurality of deoxyribonucleic acids. In some embodiments, the $S_k$ oligonucleotide is at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 nucleotides long. In some embodiments, the $S_k$ oligonucleotide is between 10-30, between 10-50, between 10-70, between 10-100, between 20-50, between 20-70, between 20-100, between 30-50, between 30-70, between 30-100, between 40-70, between 40-100, between 50-70, between 50-100, between 60-70, between 60-80, between 60-90, or between 60-100 nucleotides in length.

In some embodiments, the $S_k$ oligonucleotide is no more than 5, no more than 10, no more than 15, no more than 20, no more than 25, no more than 30, no more than 35, no more than 40, no more than 45, no more than 50, no more than 55, no more than 60, no more than 65, no more than 70, no more than 75, no more than 80, no more than 85, no more than 90, no more than 95, or no more than 100 nucleotides long.

In some embodiments, the $S_k$ oligonucleotide comprises one or more synthetic nucleotides. In some embodiments, the $S_k$ oligonucleotide is wholly single stranded. In some embodiments, the $S_k$ oligonucleotide is partially double stranded.

In some embodiments, the binding region of the $S_k'$ oligonucleotide is complimentary to at least a portion of said first oligonucleotide $S_k$. In some embodiments, the binding region of the $S_k'$ oligonucleotide is at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 nucleotides long. In some embodiments, the first binding region of the $S_k'$ oligonucleotide is between 10-30, between 10-50, between 10-70, between 10-100, between 20-50, between 20-70, between 20-100, between 30-50, between 30-70, between 30-100, between 40-70, between 40-100, between 50-70, between 50-100, between 60-70, between 60-80, between 60-90, or between 60-100 nucleotides in length.

In some embodiments, the binding region of the $S_k'$ oligonucleotide is no more than 5, no more than 10, no more than 15, no more than 20, no more than 25, no more than 30, no more than 35, no more than 40, no more than 45, no more than 50, no more than 55, no more than 60, no more than 65, no more than 70, no more than 75, no more than 80, no more than 85, no more than 90, no more than 95, or no more than 100 nucleotides long.

In some embodiments, the binding region of said $S_k'$ oligonucleotide comprises one or more synthetic nucleotides. In some embodiments, the $S_k'$ oligonucleotide comprises a plurality of ribonucleic acids. In some embodiments, the $S_k'$ oligonucleotide comprises a plurality of deoxyribonucleic acids.

In some embodiments, the $S_k'$ oligonucleotide is at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 nucleotides long. In some embodiments, the second oligonucleotide is between 10-30, between 10-50, between 10-70, between 10-100, between 20-50, between 20-70, between 20-100, between 30-50, between 30-70, between 30-100, between 40-70, between 40-100, between 50-70, between 50-100, between 60-70, between 60-80, between 60-90, or between 60-100 nucleotides in length. In some embodiments, the $S_k'$ oligonucleotide is no more than 5, no more than 10, no more than 15, no more than 20, no more than 25, no more than 30, no more than 35, no more than 40, no more than 45, no more than 50, no more than 55, no more than 60, no more than 65, no more than 70, no more than 75, no more than 80, no more than 85, no more than 90, no more than 95, or no more than 100 nucleotides long.

In some embodiments, one or more compounds are introduced to control or modify the TSA reaction. Examples of such compounds and TSA workflows are described, for example, in U.S. Pat. Nos. 6,372,937 and 6,828,109, and in U.S. Patent Application Publication Nos. 2017/0226572 and 2005/0003462, the entire contents of each of which are incorporated by reference herein.

In some embodiments, the dye that is conjugated to an oligonucleotide is a fluorophore, a stain, a quantum dot, or a chromogenic compound. Suitable dyes include, but are not limited to, R6G, DCC, Texas Red®, FITC, Alexa Fluor® 488, Alexa Fluor® 568, Alexa Fluor® 594, Alexa Fluor® 633, Alexa Fluor® 750, Cy3, Cy 3.5, Cy5, Cy 5.5, Cy7, coumarin, rhodamine, 5-(chlorosulfonyl)-2-(2,3,6,7,12,13, 16,17-octahydro-1H,5H,11H,15H-pyrido[3,2,1-ij]quinolizino[1',9': 6,7,8]chromeno[2,3-f]quinolin-4-ium-9-yl)benzenesulfonate, dilithium 5-carboxy-2-(3,6-diamino-4,5-disulfonato-9-xantheniuminbenzoate, dilithium 4-carboxy-2-(3,6-diamino-4,5-disulfonato-9-xantheniumyl)benzoate, [6-(2-carboxy-5-{[(2,5-dioxo-1-pyrrolidinyl)oxy]carbonyl}phenyl)-2,2,10,10-tetramethyl-8-(sulfomethyl)-10,11-dihydro-2H-pyrido[3',2': 6,7]chromeno[3,2-g]quinolin-1-ium-4-yl]methanesulfonate, [6-(2-carboxy-4-{[(2,5-dioxo-1-pyrrolidinyl)oxy]carbonyl phenyl)-1,2,2,10,10,11-hexamethyl-8-(sulfomethyl)-10,11-dihydro-2H-pyrido[3',2': 6,7]chromeno[3,2-g]quinolin-1-ium-4-yl]methanesulfonate, [6-(2-carboxy-5-{[(2,5-dioxo-1-pyrrolidinyl)oxy]carbonyl}phenyl)-1,2,2,10,10,11-hexamethyl-8-(sulfomethyl)-10,11-dihydro-2H-pyrido[3',2':6,7]chromeno[3,2-g]quinolin-1-ium-4-yl]methanesulfonate, and fluorescent and chromogenic species that are substituted variants of these species.

In some embodiments, all amplifications steps are performed first, after which one or more rounds of detection is performed via hybridization with oligo-labeled dyes, imaging, and removal of the oligo-labeled dyes as necessary. In some embodiments, the amplification is performed with the sample located elsewhere than on the microscope, which can improve utilization of that apparatus; or in order to make use of specialized processing equipment such as an auto-stainer for the amplification steps. In other embodiments, the amplification is performed with the sample on the microscope. This enables fully automated workflows where there is no need for robotic or human intervention to move the sample from one instrument or processing station to another, across the full amplification and detection process.

In other embodiments, amplification and detection steps are intermixed. In some embodiments, the steps described herein can be repeated.

In an aspect, the disclosure features methods for imaging an analyte in a biological sample, the methods including contacting the biological sample with a binding agent, where the binding agent features a binding moiety that binds to the analyte and a first nucleotide sequence, contacting the biological sample with a catalytic agent, where the catalytic agent features a second nucleotide sequence linked to an enzyme, and where the second nucleotide sequence hybridizes to the first nucleotide sequence, contacting the biological sample with a localization agent, where the localization agent features a substrate complementary to the enzyme and a third nucleotide sequence linked to the substrate, contacting the biological sample with a labeling agent, where the labeling agent features a fourth nucleotide sequence linked to an optical label, where the fourth nucleotide sequence hybridizes to the third nucleotide sequence, and exposing the biological sample to illumination light, detecting emitted light from the biological sample, and forming an image of the biological sample in which a location of the analyte is indicated by the optical label.

In another aspect, the disclosure features methods for imaging multiple analytes in a biological sample, the methods including (a) contacting the biological sample with a binding agent featuring a binding moiety that selectively binds to one of the analytes and a first nucleotide sequence, (b) contacting the biological sample with a catalytic agent, where the catalytic agent features a second nucleotide sequence linked to an enzyme, and where the second nucleotide sequence hybridizes to the first nucleotide sequence, (c) contacting the biological sample with a localization agent, where the localization agent features a substrate complementary to the enzyme and a third nucleotide sequence linked to the substrate, to deposit the third nucleotide sequence adjacent to the one of the analytes, repeating steps (a)-(c) to deposit N different third nucleotide sequences in the biological sample such that each one of the third nucleotide sequences is selectively positioned adjacent to a different one of the analytes, contacting the biological sample with M different labeling agents, where each labeling agent features a fourth nucleotide sequence linked to a different optical label, where the fourth nucleotide sequence hybridizes to only one of the third nucleotide sequences, and obtaining an image of the sample in which a location of one of the analytes is indicated by a location of one of the optical labels.

In a further aspect, the disclosure features methods for imaging an analyte in a biological sample, the methods including linking an enzyme to the analyte so that the enzyme is localized in the biological sample at a location of the analyte, contacting the biological sample with a localization agent featuring a substrate complementary to the enzyme and a first nucleotide sequence to deposit the first nucleotide sequence in the biological sample adjacent to the location of the analyte, contacting the biological sample with a labeling agent featuring a second nucleotide sequence that hybridizes to the first nucleotide sequence and an optical label, and obtaining an image of the biological sample in which the location of the analyte is represented by a location of the optical label.

Embodiments of any of the methods can include any of the following features.

The binding moiety can include an antibody, an antibody fragment, or an antibody analog. The antibody, antibody fragment, or antibody analog can include a member selected from the group consisting of an IgG antibody, an IgM antibody, a monoclonal antibody, a single chain variable fragment, and a diabody.

The first nucleotide sequence can include at least 5 nucleotides (e.g., at least 50 nucleotides). The first nucleotide sequence can include a DNA fragment. The first nucleotide sequence can include a RNA fragment. The first nucleotide sequence can include at least one synthetic nucleotide. The first nucleotide sequence can be a single-stranded sequence. The first nucleotide sequence can be at least partially double-stranded.

The second nucleotide sequence can be at least 80% complementary to the first nucleotide sequence. As used herein, a percentage of complementarity between two nucleotide sequences refers to the percentage of complementary bases between the binding regions of the two sequences. To achieve reproducible binding, a second sequence can be at least 70% (e.g., at least 75%, at least 80%, at least 85%, at least 90%, at least 95%, at least 98%, at least 99%) complementary to a first sequence.

The second nucleotide sequence can include at least 5 nucleotides. The first and second nucleotide sequences can include different numbers of nucleotides.

The enzyme can include horseradish peroxidase or a derivative thereof. The enzyme can include a compound that mimics horseradish peroxidase. The compound can include a hemin-containing complex. The compound can include hematin. The enzyme can include soybean peroxidase.

The third nucleotide sequence can be the same as the first nucleotide sequence. The third nucleotide sequence can be different from the first nucleotide sequence. The third nucleotide sequence can include at least 5 nucleotides (e.g., at least 50 nucleotides). The third nucleotide sequence can include a DNA fragment. The third nucleotide sequence can include a RNA fragment. The third nucleotide sequence can include at least one synthetic nucleotide. The third nucleotide sequence can be a single-stranded sequence. The third nucleotide sequence can be at least partially double-stranded.

The fourth nucleotide sequence can be at least 80% complementary to the third nucleotide sequence. The fourth nucleotide sequence can include at least 5 nucleotides. The third and fourth nucleotide sequences can include different numbers of nucleotides.

The optical label can include a fluorescent species. The optical label can include a chromogenic stain.

The biological sample can be a tissue sample. The tissue sample can be a fresh tissue sample, a frozen tissue sample, or a formalin-fixed, paraffin-embedded (FFPE) tissue sample.

The analyte can include a protein. The analyte can include a peptide or peptide fragment.

The methods can include, prior to exposing the biological sample to illumination light, contacting the biological sample with a counterstain, and exposing the biological sample to illumination light, detecting emitted light from the biological sample, and forming a second image of the sample that shows the location of the counterstain in the biological sample. The counterstain can include DAPI.

A ratio of an amount of the fourth nucleotide sequence to an amount of the first nucleotide sequence in the biological sample can be greater than 1 (e.g., greater than 5, greater than 50).

The binding agent can be a first binding agent, the catalytic agent can be a first catalytic agent, the localization agent can be a first localization agent, the labeling agent can be a first labeling agent, the analyte can be a first analyte, and the binding moiety can be a first binding moiety, and the methods can include contacting the biological sample with a second binding agent, where the second binding agent features a second binding moiety that binds to a second analyte in the biological sample and a fifth nucleotide sequence. The second analyte can be different from the first analyte. The second analyte can include a protein, a peptide, or a peptide fragment. The methods can include contacting the biological sample with the first and second binding agents at the same time. The methods can include contacting the biological sample with the first and second binding agents sequentially.

The catalytic agent can be a first catalytic agent, the enzyme can be a first enzyme, the localization agent can be a first localization agent, the substrate can be a first substrate, the labeling agent can be a first labeling agent, and the optical label can be a first optical label, and the methods can include contacting the biological sample with a second catalytic agent, where the second catalytic agent features a sixth nucleotide sequence linked to a second enzyme, and where the sixth nucleotide sequence hybridizes to the fifth nucleotide sequence, contacting the biological sample with a second binding agent, where the second binding agent features a second substrate complementary to the second enzyme and a seventh nucleotide sequence linked to the second substrate, and contacting the biological sample with a second labeling agent, where the second labeling agent features an eighth nucleotide sequence linked to a second optical label, where the eighth nucleotide sequence hybridizes to the seventh nucleotide sequence. The first and fifth nucleotide sequences can be the same. The first and fifth nucleotide sequences can be different. The second and sixth nucleotide sequences can be the same or different. The third and seventh nucleotide sequences can be different. The fourth and eighth nucleotide sequences can be different.

The first and second optical labels can be different. The second binding moiety can include an antibody, an antibody fragment, or an antibody analog. The antibody, antibody fragment, or antibody analog can include a member selected from the group consisting of an IgG antibody, an IgM antibody, a monoclonal antibody, a single chain variable fragment, and a diabody. The fifth nucleotide sequence can include at least 5 nucleotides. The fifth nucleotide sequence can include at least one member selected from the group consisting of a DNA fragment and a RNA fragment. The fifth nucleotide sequence can include at least one synthetic nucleotide. The fifth nucleotide sequence can be a single-stranded sequence. The fifth nucleotide sequence can be at least partially double-stranded.

The sixth nucleotide sequence can be at least 80% complementary to the fifth nucleotide sequence. The sixth nucleotide sequence can include at least 5 nucleotides. The fifth and sixth nucleotide sequences can include different numbers of nucleotides.

The first and second enzymes can be different. The second enzyme can include horseradish peroxidase, a derivative or horseradish peroxidase, a compound that mimics horseradish peroxidase, a hemin-containing complex, and hematin. The second enzyme can include soybean peroxidase. The seventh nucleotide sequence can be the same as the fifth nucleotide sequence. The seventh nucleotide sequence can be different from the fifth nucleotide sequence. The seventh nucleotide sequence can include at least 5 nucleotides. The seventh nucleotide sequence can include at least one member selected from the group consisting of a DNA fragment and a RNA fragment. The seventh nucleotide sequence can include at least one synthetic nucleotide. The seventh nucleotide sequence can be a single-stranded sequence. The seventh nucleotide sequence can be at least partially double-stranded.

The eighth nucleotide sequence can be at least 80% complementary to the seventh nucleotide sequence. The eighth nucleotide sequence can include at least 5 nucleotides. The seventh and eighth nucleotide sequences can include different numbers of nucleotides.

The second optical label can include a fluorescent species. The second optical label can include a chromogenic stain.

A ratio of an amount of the eighth nucleotide sequence to an amount of the fifth nucleotide sequence in the biological sample can be greater than 1 (e.g., greater than 50). The ratio of the amount of the eighth nucleotide sequence to the amount of the fifth nucleotide sequence in the biological sample can be different from a ratio of the amount of the fourth nucleotide sequence to the amount of the first nucleotide sequence in the biological sample. The ratio of the amount of the eighth nucleotide sequence to the amount of the fifth nucleotide sequence in the biological sample may not be greater than 1. The ratio of the amount of the eighth nucleotide sequence to the amount of the fifth nucleotide sequence in the biological sample can be greater than 1, and the ratio of the amount of the fourth nucleotide sequence to the amount of the first nucleotide sequence in the biological sample can be greater than 1.

The methods can include, prior to contacting the biological sample with the second labeling agent, removing the first labeling agent from the biological sample. The methods can include removing the first labeling agent from the biological sample prior to contacting the biological sample with the second localization agent. The methods can include removing the first labeling agent from the biological sample prior to contacting the biological sample with the second catalytic agent. The methods can include removing the first labeling agent from the biological sample prior to contacting the biological sample with the second binding agent. The methods can include removing the first labeling agent from the biological sample by dehybridizing the fourth nucleotide sequence from the third nucleotide sequence.

The image of the biological sample can be a first image, and the methods can include exposing the biological sample to illumination light, detecting emitted light from the biological sample, and forming a second image of the biological sample in which a location of the second analyte is indicated by the second optical label. The first optical label can be present in the biological sample when the biological sample is exposed to the illumination light to form the second image of the biological sample.

The methods can include removing the first optical label from the biological sample prior to exposing the biological sample to the illumination light to form the second image of the biological sample. Removing the first optical label from the biological sample can include dehybridizing the fourth nucleotide sequence from the third nucleotide sequence.

The methods can include, after contacting the biological sample with the localization agent and prior to contacting the biological sample with the labeling agent, contacting the biological sample with a second catalytic agent, where the second catalytic agent features a fifth nucleotide sequence linked to a second enzyme, and where the fifth nucleotide sequence hybridizes to the third nucleotide sequence, contacting the biological sample with a second localization agent, where the second localization agent features a second substrate complementary to the second enzyme and a sixth nucleotide sequence linked to the second substrate, and where the fourth nucleotide sequence of the labeling agent hybridizes to the sixth nucleotide sequence. The fifth nucleotide sequence and the first nucleotide sequence can be the same. The sixth nucleotide sequence and the fourth nucleotide sequence can be the same. The second enzyme can be selected from the group consisting of horseradish peroxidase and derivatives thereof, hemin-containing complexes, hematin, and soybean peroxidase.

Embodiments of the methods can also include any of the other features described herein, including combinations of features described in connection with different embodiments, except as expressly stated otherwise.

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Like elements in the figures are labeled with common reference signs.

DETAILED DESCRIPTION

Overview

Figure 1A:
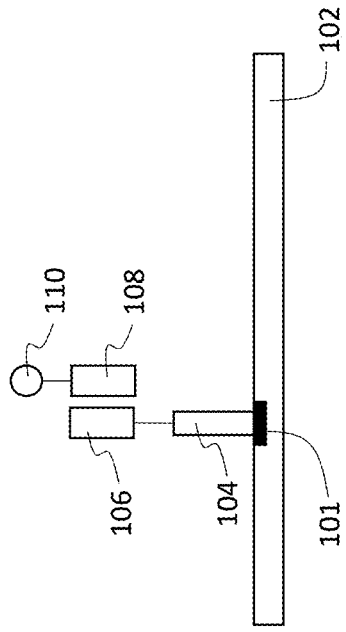
FIG. 1A is a schematic diagram showing binding of a binding agent that includes a primary antibody conjugated to a first oligonucleotide to a sample.

Immunofluorescence techniques can be used to observe multiple antigen targets in a single sample, for example to visualize or measure expression of several protein, peptide, or other amino acid-containing targets in a given cell or tissue section. This so-called multiplexed immunofluorescence can be done in several ways. For example, one technique involves contacting the sample with several directly labeled primary antibodies, where each primary antibody can target an antigen of interest and can be conjugated to a different fluorescent dye. In such a method, antibodies can be applied in a single step, however the dyes are distinguishable from one another during imaging, so the number of antigen targets—the degree of multiplexing—is limited by the number of dyes that can be resolved. Also, because there is no amplification mechanism, the number of dye molecules per antigen is set by the dye-antibody conjugation and can be relatively low.

Indirect labeling can be used to obtain brighter signals. In that technique, secondary antibodies of different species can bind to the various primary antibodies, and fluorescent dyes can bind to the secondary antibodies. This may provide the potential for amplification through secondary binding at multiple sites, but it is a more complex approach than direct labeling since it may require each primary antibody to have been raised in a different species, or alternatively that the secondary antibodies may recognize different antibodies from the same species.

Serial staining techniques have been developed wherein a sample can be contacted with a single primary antibody targeting a first antigen. A secondary antibody conjugated to horseradish peroxidase (HRP) can be introduced and localize to the primary antibody sites. Tyramide signal amplification (TSA) can be used to deposit dye molecules near these sites through a reaction catalyzed by HRP. The TSA reaction can produce relatively high amplification. After dye deposition, the primary and secondary antibodies may be stripped or denatured, but the dye remains largely bound to the sample. The process can be repeated several times, and a different primary antibody targeting a different antigen to deposit a different dye may be used each time. When the dyes have been deposited, the sample is imaged.

Because it is a serial approach with only one primary antibody active at a time, there are no cross-species reactivity concerns. This is of great practical benefit since antibodies can be selected without concern for the animal species they were raised against. However, because the dyes remain durably bound to the sample, the degree of multiplexing is limited by the number of dyes that can be reliably distinguished from one another in a single imaging round.

In some embodiments, multiple primary antibodies can be conjugated to oligomers. For example, several antibodies may be used, each targeting an antigen of interest, wherein each may be conjugated to a different oligomer. The oligomer sequences can be chosen or engineered for low cross-hybridization between the different oligomers. The sample can be contacted with the primary antibodies, which can localize at the antigen sites according to their type. Fluorescent dyes or other detection moieties such as quantum dots can be conjugated to oligomer sequences keyed to those used for the various primary antibodies. One or more of these may be brought into contact with the sample under conditions that can promote hybridization of a detection-linked oligomer to its antibody-linked counterpart. In this way, the detection moieties can localize at the antigen sites of the associated antibodies, and the sample can be imaged. Herein this is termed unamplified oligo-mediated detection. Aspects of such methods are described, for example, in U.S. Pat. Nos. 9,909,167 and 10,370,698, the entire contents of which are incorporated by reference.

The detection-linked oligo chains can be removed by creating conditions that favor dehybridization and performing washing steps. Many primary antibodies can be used in a single experiment, each with a distinct oligo sequence, with the corresponding detection-linked oligos being hybridized, imaged, and removed in groups. In some workflows, the imaging step may only distinguish the number of dyes present in any one group, while overall measurement can achieve high multiplexing levels through repetition.

Sample Labeling and Imaging

This disclosure features methods for sample labeling and imaging that involve enzyme-mediated amplification of signals that correspond to particular target analytes in a sample. In some embodiments, the methods include contacting a biological sample with an antibody or antibody fragment that is conjugated to a first oligonucleotide $S_i$; contacting said first oligonucleotide with a binding region of a second oligonucleotide $S_i'$; wherein the binding region of the second oligonucleotide $S_i'$ is complementary to at least a portion of the first oligonucleotide $S_i$, where the second oligonucleotide $S_i'$ is conjugated to an enzyme; such that the enzyme mediates the deposition of a substance on the biological sample via the TSA reaction. This substance is itself a third oligonucleotide $S_k$ which is complementary to at least a portion of a fourth oligonucleotide $S_k'$ that is conjugated to a dye which is imaged using a microscope or similar apparatus.

In this discussion, the subscript i in $S_i$ denotes a first oligonucleotide sequence, and its use in connection with a selected target in the sample being imaged. The notation $S_i'$ indicates a second oligonucleotide sequence that is complementary to $S_i$ which is capable of selectively binding with $S_i$ along at least a portion of its length. $S_i$ is drawn from an orthogonal set of sequences, meaning $S_i'$ does not hybridize under stringent conditions with any other sequence $S_j$ in the set where $j \neq i$.

The subscript k in $S_k$ denotes an oligonucleotide sequence and its use in connection with a selected target in the sample being imaged. The notation $S_k'$ indicates an oligonucleotide sequence that is complementary to $S_k$ which is capable of selectively binding with $S_k$ along at least a portion of its length. $S_k$ is drawn from an orthogonal set of sequences, meaning $S_k'$ does not hybridize under stringent conditions with any other sequences $S_m$ in the set where $k \neq m$.

When describing amplified detection of multiple targets in accordance with the present disclosure, the same notation of subscripts and primes is used in connection with each target, but the actual sequences that $S_i$ and $S_k$ refer to are different for each target. Thus, in a multiplexed experiment with M different targets for which amplification is used, each target will have an antibody that is conjugated to an oligonucleotide denoted by $S_i$, but the actual sequence that $S_i$ refers to will be different for each antibody. Similarly, the TSA reaction associated with that target deposits an oligonucleotide sequence denoted by $S_k$, but the actual sequence $S_k$ refers to will be different for each target. Similarly, oligo-labeled HRP used in connection with that target will have a sequence that is denoted herein as $S_i'$ but the actual sequence that $S_i'$ refers to will be different for each target; and the oligo-labeled dye will have a sequence that is denoted $S_k'$ but the actual sequence that $S_k'$ refers to will be different for each target.

Techniques exist for designing or choosing a set of sequences $\{S_1, S_2 \ldots S_N\}$ that are orthogonal and have a low probability of binding selectively with naturally occurring oligonucleotide sequences. See, for example, U.S. Pat. No. 10,370,698, which lists example sets of complementary sequences that satisfy these conditions.

The biological sample can be contacted with two or more (e.g., 3 or more, 4 or more, 5 or more, 6 or more, 8 or more, 10 or more, 12 or more, 15 or more, 20 or more, 30 or more, 40 or more, 50 or more, 60 or more, 80 or more, or even more) antibodies, antibody fragments, or a combination thereof. The sample can be contacted with a cocktail of all the antibodies or antibody fragments, or combinations of multiple subsets of the total number of antibodies. In addition to the time savings and simplification obtained from using a single such incubation, it can yield improved detection of co-located targets in the sample. Without wishing to be bound by theory, a single cocktailed incubation appears to reduce or eliminate systematic interference between antibodies that bind to targets which are adjacent or overlapping on the sample.

Antigen retrieval, blocking and wash steps related to antibody incubation can be employed in accordance with normal immunohistochemical practice. The specific steps, compounds used, times, temperatures, and sequence of actions can be optimized based on the targets being imaged in order to obtain good sensitivity, localization, selectivity, or other criteria of interest.

Each of the one or more antibodies, antibody fragments, or combination thereof is conjugated to a first oligonucleotide $S_i$ which is unique to that antibody or antibody fragment. After contacting the antibody or antibody fragment to the sample, the first oligonucleotide can be contacted with a second oligonucleotide $S_i'$. For example, the first oligonucleotide can hybridize to the second oligonucleotide, such as by complimentary base pairing. Each first oligonucleotide $S_i$ can correspond to a unique second oligonucleotide $S_i'$. This can be accomplished via a barcoding system involving an orthogonal set of sequences {$S_1, S_2 \ldots S_N$} as described earlier.

In some instances, the first oligonucleotide $S_i$ is coupled with the antibody or fragment indirectly, for example via an additional linker oligonucleotide. Other methods of indirect coupling include binding of a first oligonucleotide $S_i$ that is conjugated to a secondary antibody, nanobody, or other entity that specifically targets the primary antibody, thereby linking the primary antibody to the first oligonucleotide indirectly.

Each second oligonucleotide $S_i'$ is conjugated to an enzyme capable of mediating the deposition of a detectable substance on the biological sample. In some preferred embodiments, the second oligonucleotide $S_i'$ can be conjugated to a horseradish peroxidase (HRP) enzyme. In other embodiments, the second oligonucleotide $S_i'$ is conjugated to a polymer comprising several HRP molecules. In some embodiments, the enzyme can be a hemin-containing complex which can mimic HRP, such as hematin. In some embodiments, the enzyme can be soybean peroxidase. In some instances, the second oligonucleotide is coupled with the enzyme indirectly, for example via an additional linker oligonucleotide or a click-chemistry system.

Stringent or near-stringent conditions can be employed to ensure that little or no binding occurs at sites other than the intended $S_i$ barcodes on the target antibodies. Other oligonucleotide sequences can be applied as well, which have no associated enzyme and do not bind selectively with the intended binding target $S_i$, to further reduce the likelihood of nonspecific binding of the enzyme to the sample.

Excess catalytic agent molecules which correspond to oligonucleotide-labeled enzymes can be removed from the sample by washing, after which the enzyme is localized only or primarily in the vicinity of the associated primary antibody.

The TSA reaction is used to deposit an oligonucleotide $S_k$ on the sample. An oligo sequence $S_k$ is conjugated to a substrate which can be a tyramine compound, or p-hydroxycinnamic acid, or another substrate that is catalyzed by HRP to bind to the sample per the TSA mechanism. The coupling between the oligo sequence $S_k$ and the substrate material can be indirect, for example via an additional linker oligonucleotide, or by another mechanism.

A localization agent that includes an oligonucleotide-labeled enzyme substrate with sequence $S_k$ is introduced to the sample while oligonucleotide-linked enzyme with sequence $S_i'$ is bound through hybridization to an oligonucleotide-linked antibody with sequence $S_i$. This results in deposition of oligo sequences $S_k$ nominally only at locations corresponding to this antibody.

As mentioned above, the deposition of the localization agent results in amplification of the imaging signal that is associated with a particular target analyte. The amplification factor is denoted by α in this discussion and describes the number of molecules with oligonucleotide sequence $S_k$ deposited onto the sample per antibody molecule localized at a sample target site. Since each of the deposited oligonucleotides of sequence $S_k$ can be labeled to producing an imaging signal (e.g., a fluorescent signal or a signal corresponding to light absorption, transmission, or reflection), the number of such oligonucleotides of sequence $S_k$ relative to each target analyte molecule corresponds to the amplification factor or degree of amplification, a.

Because each target analyte molecule is labeled with a primary antibody that is linked to a single oligonucleotide molecule of sequence $S_i$, the amplification factor α effectively corresponds to a ratio of the amount or concentration of the oligonucleotides of sequence $S_k$ in the sample to the amount or concentration of the oligonucleotides of sequence $S_i$ in the sample. The ratio of the amounts or concentrations (i.e., the amplification factor) can be 1.1 or more (e.g., 1.5 or more, 2.0 or more, 3.0 or more, 4.0 or more, 5.0 or more, 7.0 or more, 10.0 or more, 20.0 or more, 30.0 or more, 40.0 or more, 50.0 or more, 60.0 or more, 70.0 or more, 80.0 or more, 90.0 or more, 100.0 or more, 200.0 or more, 500.0 or more, 1000 or more, 5000 or more, 10000 or more, or even more). The amplification factor α can be adjusted to balance signal levels between multiple antibodies; to achieve a desired staining pattern; or for other purposes based on the assay being performed.

The enzyme-mediated amplification process can be controlled through adjusting the concentration of the oligonucleotide-labeled enzyme substrate in the localization agent; the reaction time; the reaction temperature; and replacement or replenishment of the oligonucleotide-conjugated enzyme substrate. It can also be modified by addition of compounds such as an inorganic salt, or an organic enhancing compound such as those described in U.S. Pat. No. 6,372,937, the entire contents of which are incorporated by reference. The degree of amplification can be adjusted separately for each target analyte by separately performing enzyme-mediated deposition of localization agents associated with each target analyte.

Under some conditions, the TSA reaction leads to dimerization of the enzyme substrate molecules rather than deposition onto the sample. This can occur when the density of enzyme molecules, or of oligonucleotide-labeled enzyme substrate molecules, is too high. Reduction of one of these factors, or both, can reduce the effect of dimerization and produce greater levels of deposition. For example, one may reduce the concentration of oligonucleotide-labeled enzyme substrate; or use a non-polymer HRP enzyme in place of polymer HRP enzyme.

A deposition cycle can be performed for each antibody in turn, using oligonucleotide-linked enzymes (e.g., HRP) with an oligonucleotide sequence $S_i'$ corresponding to the antibody linked to an oligonucleotide of sequence $S_i$, depositing an oligonucleotide sequence $S_k$ on the sample. This is repeated for each antibody for which amplified detection is sought, where each type of antibody is linked to a different oligonucleotide with a different sequence $S_i$.

In some embodiments, the oligonucleotide with sequence $S_k$ deposited for a given antibody is the same as the sequence $S_i$ conjugated to that antibody. In such embodiments, the result of the deposition step is to bind multiple oligonucleotide molecules to the sample adjacent to the antibody, having the same sequence as the oligonucleotide sequence conjugated to that antibody.

In certain embodiments, the sequence $S_k$ deposited for a given antibody is different from the sequence $S_i$ conjugated to that antibody. In such embodiments, the effect of the deposition step is to bind multiple oligonucleotide molecules to the sample adjacent to the antibody, having a different sequence from the oligonucleotide sequence conjugated to that antibody.

Oligonucleotide sequences $S_k$ deposited on the sample can be detected using a dye molecule conjugated to oligonucleotide sequence $S_k'$ that selectively hybridizes with $S_k$ along at least part of its length.

Detection includes introducing a labeling agent that includes oligonucleotide-labeled dye molecules; providing stringent or near-stringent hybridization conditions under which oligonucleotide sequences $S_k'$ conjugated with the dye molecules selectively hybridize with the oligonucleotides having sequences $S_k$ deposited on the sample or conjugated to antibodies; removing oligonucleotide-labeled dye molecules that did not hybridize; optionally applying a counterstain such as DAPI; imaging the sample using a microscope to form an image of the dye molecules; and optionally, removing the oligo-labeled dye molecules by dehybridization and washing steps.

Taken together, the steps of binding oligonucleotide-labeled dye molecules at sites on the sample where complementary localization agents are present, applying a counterstain, imaging the sample, and removing the dye molecules form one cycle of detection.

As mentioned above, an important aspect of certain methods described herein is that amplified detection of target analytes can be performed, followed by removal from the sample of the labeling agent that generates that signals observed during sample imaging. As a result, multiple cycles of sample labeling, imaging, and optionally, label removal can be performed in series. Since the dyes used each cycle can be removed via dehybridization and washing steps, they do not interfere with labeling imaging in subsequent cycles. Overall a high degree of multiplexing to detect N target analytes can be achieved through successive cycles of labeling and detection, where a smaller number of dyes B, or even a single dye (B=1), is used in each cycle.

In general, the number of target analytes N that can be detected using the methods described herein, N, is 1 or more (e.g., 2 or more, 3 or more, 4 or more, 5 or more, 6 or more, 8 or more, 10 or more, 12 or more, 15 or more, 20 or more, 25 or more, 30 or more, 35 or more, 40 or more, 45 or more, 50 or more, or even more).

The number of dyes B that are detected in a single imaging step can be 1 or more, (e.g., 2 or more, 3 or more, 4 or more, 5 or more, 6 or more, 8 or more, 10 or more, 15 or more, 20 or more, 30 or more, 40 or more, 50 or more, 70 or more, or even more).

The number of different types of labeling agents, M, that can be deposited in the sample to detect target analytes can be 1 or more (e.g., 2 or more, 3 or more, 4 or more, 5 or more, 6 or more, 8 or more, 10 or more, 12 or more, 15 or more, 20 or more, 25 or more, 30 or more, 35 or more, 40 or more, 45 or more, 50 or more, or even more). In some embodiments, M is less than or equal to N.

In some embodiments, amplified deposition of localization agents that include oligonucleotides is performed for every target being imaged. In certain embodiments, amplified deposition of localization agents that include oligonucleotides is performed for only a single target, or for a subset of the N targets being imaged.

When amplification is performed, detection of a target analyte can be done at any point after the deposition of the localization agent for that target. It is possible to alternate between deposition steps and detection steps, and in some embodiments, one or more deposition steps can be performed to introduce one or more different types of localization agents associated with different target analytes, and one or more detection steps can be performed to label and detect the localization agents, followed by further cycles of deposition and detection.

In some embodiments, localization agents can be deposited in the sample for all target analytes of interest before any detection steps (e.g., introduction of labeling agents and imaging of the sample) are performed. Localization agents can be deposited using specialized, purpose-built instruments such as autostainers, microfluidic systems with staining chambers, and other systems. Such systems dispense reagents automatically, and control temperature, processing time, and flow rates without user intervention. One advantage of such systems is that a sample is not cycled repeatedly between a staining apparatus and an imaging station. Suitable systems for applying the reagents and methods herein are described, for example, in U.S. patent application Ser. No. 16/902,215, and in U.S. Pat. Nos. 6,735,531 and 7,226,788, the entire contents of each of which are incorporated herein by reference.

Detection can be done for one analyte at a time, but can also be done for 2, 3, 4, 5, 6, or even more analytes at a time, along with one or more counterstains that bind non-specifically to regions in the sample (e.g., one or more tissue counterstains, one or more nuclear counterstains). Different labeling agents each with an oligonucleotide-labeled dye molecule are introduced and hybridized at once, and because the nucleotide sequences $S_k'$ of the labeling agents are orthogonal as discussed previously, each dye molecule localizes at a corresponding antibody that binds to only one of the target analytes (or, equivalently, its associated TSA-deposited localization agent with an oligonucleotide having sequence $S_k$ in the sample). The number of dyes, the dyes selected, and the imaging process are chosen to ensure that the signals associated with each dye, and hence, each target analyte, can be distinguished from one another in the resulting image.

It is instructive to compare the methods described herein with other serial multiplexing methods. A method termed Sequential ImmunoPeroxidase Labeling and Erasing (SIMPLE, G. Glass, J. Papin, J Mandell, J. Histochem Cytochem 2009 Oct; 57 (10): 899:905) involves serial rounds of IHC using 3-amino-9-ethylcarbazole (AEC); this stain is imaged and then dissolved using alcohol. Each IHC round provides a view of a single marker, and requires blocking, primary antibody incubation, washing, secondary antibody incubation, further washing, and staining; the sample is then imaged, washed in water, 3 dilutions of ethanol, water, potassium permanganate, and water. These steps take a total time of almost 3 hours per marker, so performing a 12-plex assay would require 36 hours of sample processing, excluding the time spent imaging the sample twelve times.

A multiplexed imaging method is described in U.S. Pat. No. 7,729,125 where a normal prostate sample was imaged using 11 immuno-markers and DAPI. It included 2 rounds of two-channel indirect IHC, followed by 7 rounds of directly labeled IHC, with erasure of the dyes between each staining round using an NaOH solution, followed by washing in PBS. Each indirect IHC round took approximately 2 hours, each direct IHC round took approximately 1 hour, and the erasure steps took in excess of 15 minutes each. Four markers had signal amplification via secondary antibodies, and seven rounds provided no amplification. Overall, a total of 14 hours of sample processing was required, excluding the time spent imaging the sample nine times.

The methods described herein can be performed with a single incubation step for all primary antibodies. Amplified TSA-deposition can be performed individually for each target analyte where amplification is desired, and takes approximately 30 minutes per target analyte, including hybridization, washes, TSA deposition, washing and dehybridization. Detection can be done for four species per cycle or more; for example, using 4 dyes (for example, the dyes Opal 520, Opal 570, Opal 620, Opal 690, obtained from Akoya Biosciences, Inc., Menlo Park, CA) along with a DAPI counterstain, and imaging can be performed using a Vectra Polaris instrument (available from Akoya Biosciences, Inc.) The time required for each detection round is approximately 30 minutes, including about 10 minutes for the imaging. Excluding primary incubation, the overall sample processing time for this example is three and a half hours when 4 species are amplified, or seven and a half hours when 12 species are amplified.

This comparison illustrates several beneficial aspects of the methods described herein, including the option to use of single incubation with a cocktail of all primary antibodies; the capability to image a high number N of targets with amplification; the option to use amplification for some targets and not for others; the ability to attain high amplification for markers where that is desired; the ability to label and image multiple targets B in a single detection round; and high speed overall.

In embodiments using fluorescent dye molecules, imaging can be performed using fluorescence microscopy. This can be done using wide-field epi-fluorescence methods or it can use techniques such as confocal imaging, super-resolution imaging, multispectral imaging, two-photon microscopy, or total-internal-reflection microscopy. The imaging system used to obtain images can include upright and/or inverted microscopes, digital slide scanners, or custom apparatus.

In embodiments using chromogenic dye molecules, imaging can be done using brightfield microscopy. This can be done using a white light source and transmitted-light optics or it can use techniques such as laser-scanning, narrowband imaging, or multispectral imaging.

In certain embodiments, serial amplification cycles can be performed for each of one or more target analytes. For example, a primary antibody conjugated to oligonucleotide sequence $S_i$ is contacted by an oligonucleotide-labeled enzyme such as HRP conjugated to $S_i'$. An oligonucleotide-labeled enzyme substrate with sequence $S_k$ is introduced into the sample and oligonucleotide molecules with sequence $S_k$ are deposited on the sample through the TSA mechanism, with amplification factor of $\alpha_1$, catalyzed by the enzyme associated with the primary antibody.

The oligonucleotide-labeled enzyme with sequence $S_i'$ is optionally removed from the sample via dehybridization, and the sample is contacted with an oligonucleotide-labeled enzyme (such as HRP) conjugated to an oligonucleotide of sequence $S_k'$. Next, an oligonucleotide-labeled enzyme substrate with sequence $S_k$ is applied to the sample, hybridizing with the oligonucleotides of sequence $S_k'$ and depositing oligonucleotide molecules of sequence $S_k$ is deposited on the sample through the TSA mechanism, with amplification factor of as (where the amplification factor as corresponds to the amount or concentration of oligonucleotide molecules of sequence $S_k$ relative to the amount or concentration of oligonucleotide molecules of sequence $S_k'$. The deposition is catalyzed by the enzymes conjugated to the oligonucleotides of sequence $S_k$, as well as by the enzymes conjugated to the oligonucleotides of sequence $S_i'$, if those were not removed from the sample. Overall, the two deposition steps achieve an amplification of $(\alpha_1 \times \alpha_2)$.

Serial amplified deposition rounds can be used to achieve a higher overall amplification than is practical in a single deposition step and/or to finely control the degree of amplification. Although the foregoing example describes two deposition steps for amplification of the signal associated with a single target analyte, more generally any number of deposition steps (e.g., one or more, two or more, three or more, four or more, five or more, six or more, eight or more, 10 or more, or even more) deposition steps can be performed, each step involving introduction of a catalytic agent with an oligonucleotide-conjugated enzyme and a localization agent with a complementary oligonucleotide. In particular, for target analytes that are weakly expressed, multiple deposition steps can be advantageous for detection. Further, the number of deposition steps can be independently selected for each target analyte, and any two target analytes can be detected after the same number or different numbers of deposition steps for amplification.

In some embodiments, one or more cycles or steps of amplification are performed for a given target analyte, and detection is performed for that target analyte. Optionally, a decision is made (e.g., based on measured imaging signals corresponding to the target analyte) whether further amplification is desired. In at least some embodiments, one or more further cycles or steps of deposition for amplification are then performed for this target analyte, and detection is again performed. This provides two or more images of the sample with different levels of amplification. As discussed above, the number of images for a particular target analyte can be one or more (e.g., two or more, three or more, four or more, five or more, six or more, eight or more, 10 or more, or even more).

In some embodiments, the above differential amplification methodology is used to image samples having widely variable expression, for which the optimum amplification is not known prior to imaging. In other embodiments, the methodology is used to image strong expressing regions in a sample in a first image, and to image more weakly expressing regions of the same sample in a second image. In certain embodiments, comparison of the signal levels in the two images provides an assessment of the second amplification factor aa. Optionally an image is assembled from the first and second image with high dynamic range in target expression.

A biological sample can be fresh, frozen, or fixed. A biological sample can be of animal origin, such as from a human, mouse, rat, cow, pig, sheep, monkey, or rabbit.

A biological sample can be immobilized on a surface. In some embodiments, the surface can be a slide, a plate, a well, a membrane, or a film. The biological sample may be fixed using an aldehyde, an alcohol, an oxidizing agent, a mercurial, a picrate, or HOPE fixative. The biological sample may alternatively be fixed using heat fixation. Fixation may be achieved via immersion or perfusion. The biological sample may be fresh or frozen. In some preferred embodiments, the sample comprises formalin-fixed paraffin-embedded (FFPE) tissue.

In some embodiments, upon contacting the biological sample, the antibody or antibody fragment can be bound to the element of the biological sample. The antibody or antibody fragment can bind reversibly or irreversibly with the element of the biological sample.

The antibody or antibody fragment can comprise an IgG, an IgM, a polyclonal antibody, a monoclonal antibody, a scFv, a nanobody, a Fab, or a diabody. The antibody or antibody fragment can have specificity for an element of the sample such as a protein. The selection of a particular antibody from among the available candidates is made according to the needs of a given experiment, and can be based on factors such as cost, the available antibodies for that target, the specificity of each candidate antibody for that target, the amount of background (non-specific) binding, and other factors used in immunohistochemistry design. These may favor choosing one clone over another, or a monoclonal over a polyclonal (or vice versa).

For some clones, these properties change when the antibody is conjugated to oligonucleotide $S_1$. Accordingly, antibodies should be tested both by conventional IHC techniques to form an initial assessment of their behavior, and then checked after conjugation with an oligonucleotide sequence for use in this disclosure, to ensure their performance remains acceptable after conjugation.

Example Workflows

The methods described herein can be implemented in a wide variety of different workflows. FIGS. 1A-1D and 2A-2D are schematic diagrams that illustrate one example implementation of the methods. In FIG. 1A, a sample 102 is contacted with a binding agent that includes a binding moiety 104 that binds to an analyte 101 in sample 102. The binding moiety 104 is linked to a first oligonucleotide having a sequence $S_1$. Suitable binding moieties 104 include any of the binding moieties described herein that specifically bind to target analytes of interest in sample 102, such as antibodies and antibody fragments.

Figure 1B:
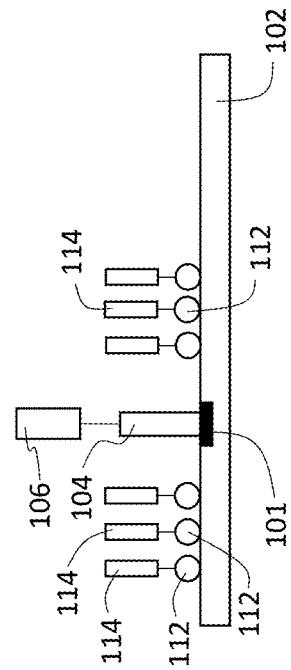
FIG. 1B is a schematic diagram showing hybridization of a catalytic agent to the binding agent of FIG. 1A.

In FIG. 1B, sample 102 is contacted with a catalytic agent that includes a second oligonucleotide 108 having a complementary sequence $S_1'$ linked to an enzyme 110. As discussed herein, suitable enzymes include HRP, soybean peroxidase, and other species that mimic the functional catalytic properties of these peroxidases. Second oligonucleotide 108 selectively hybridizes to first oligonucleotide 106 so that the catalytic agent is selectively localized at the location of the target analyte 101 in sample 102.

Figure 1C:
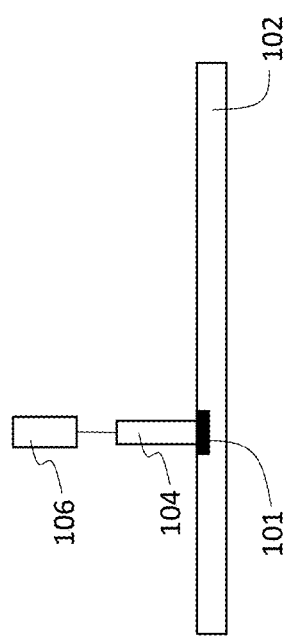
FIG. 1C is a schematic diagram showing enzyme-mediated deposition of a localization agent that includes a tyramide-conjugated oligonucleotide in a sample in the vicinity of the primary antibody of FIG. 1A.

In FIG. 1C, sample 102 is contacted with a localization agent that includes a substrate 112 complementary to enzyme 110. Substrate 112 is linked to third oligonucleotide having sequence $S_k$. Suitable substrates include, but are not limited to, tyramine and tyramine derivatives, p-hydroxycinnamic acid and derivatives thereof, as described herein. The catalytic reaction between enzyme 110 and substrate 112 deposits multiple localization agent molecules in the sample at locations proximal to the analyte 101.

Figure 1D:
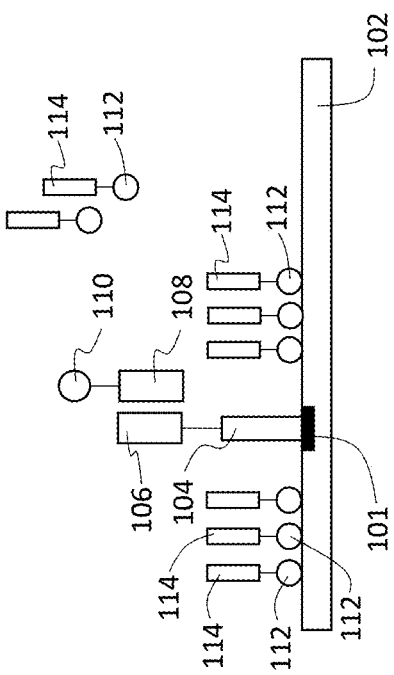
FIG. 1D is a schematic diagram showing a population of the localization agent positioned in proximity to the primary antibody of FIG. 1A in the sample.

In FIG. 1D, the catalytic agent has been removed from sample 102 via dehybridization and washing. The deposited localization agent molecules remain in the sample as shown, as they are covalently bound to the sample.

Figure 2A:
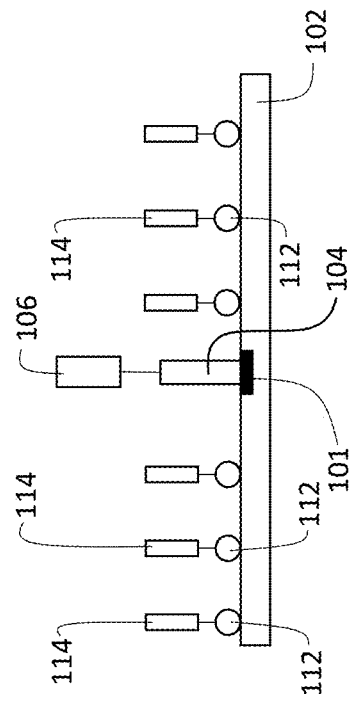
FIG. 2A is a schematic diagram showing localization agent molecules deposited in a sample in proximity to a primary antibody bound to an analyte of interest.
Figure 2B:
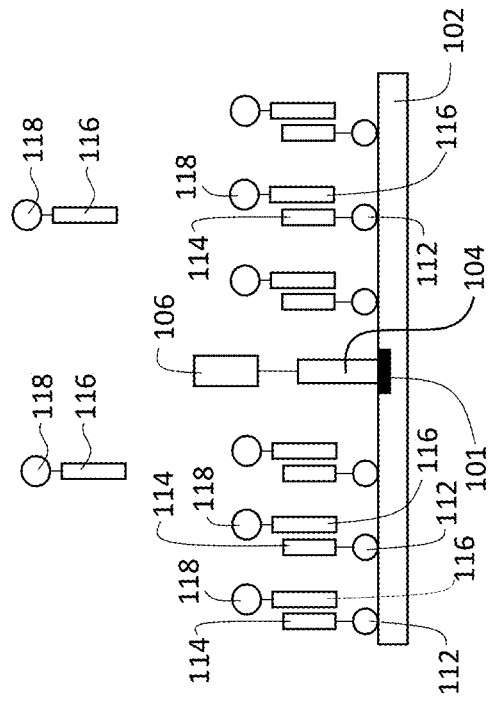
FIG. 2B is a schematic diagram showing hybridization of labeling agent molecules to localization agent molecules in the system.

FIG. 2A shows the same view of sample 102 as in FIG. 1D. In FIG. 2B, a labeling agent that includes a fourth oligonucleotide 116 having sequence $S_k'$ linked to an optical label 118 contacts the sample. The sequences of the third and fourth oligonucleotides 114 and 116 are complementary, and the fourth oligonucleotide 116 hybridizes to the third oligonucleotide 114, localizing the labeling agent in proximity to the analyte 101 in sample 102. Because multiple localization agent molecules were deposited in the sample for each analyte molecule 101, the measured signal associated with analyte 101 is amplified.

Figure 2C:
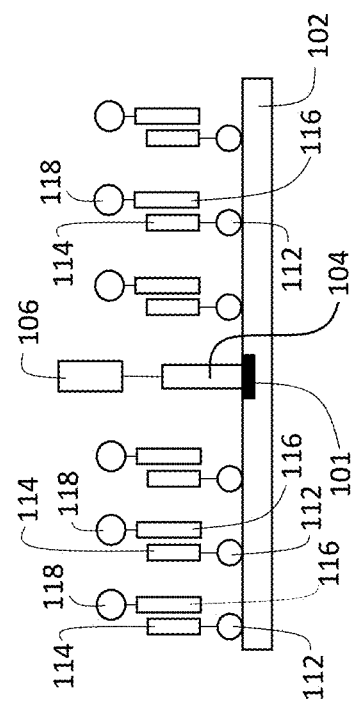
FIG. 2C is a schematic diagram showing imaging of the labeled sample in FIG. 2B.

In FIG. 2C, illumination light 120 is incident on sample 102, and optical labels 118 generate emitted light (e.g., by emitting fluorescence, or by absorbing some of the illumination light). The emitted light is detected to form an image of sample 102 in which the emitted light from optical labels 118 indicates the location of analyte 101.

Figure 2D:
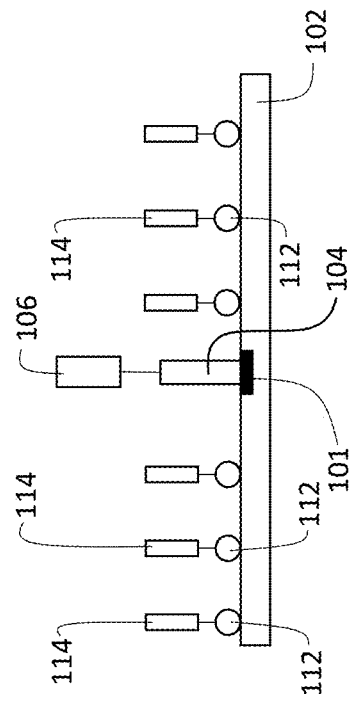
FIG. 2D is a schematic diagram showing the sample of FIG. 2B after removal of the labeling agents via dehybridization.

In FIG. 2D, the labeling agent molecules have been optionally removed by dehybridization and washing from sample 102. As described previously, additional deposition and/or detection cycles can be performed to identify additional target analytes in sample 102.

Figure 3:
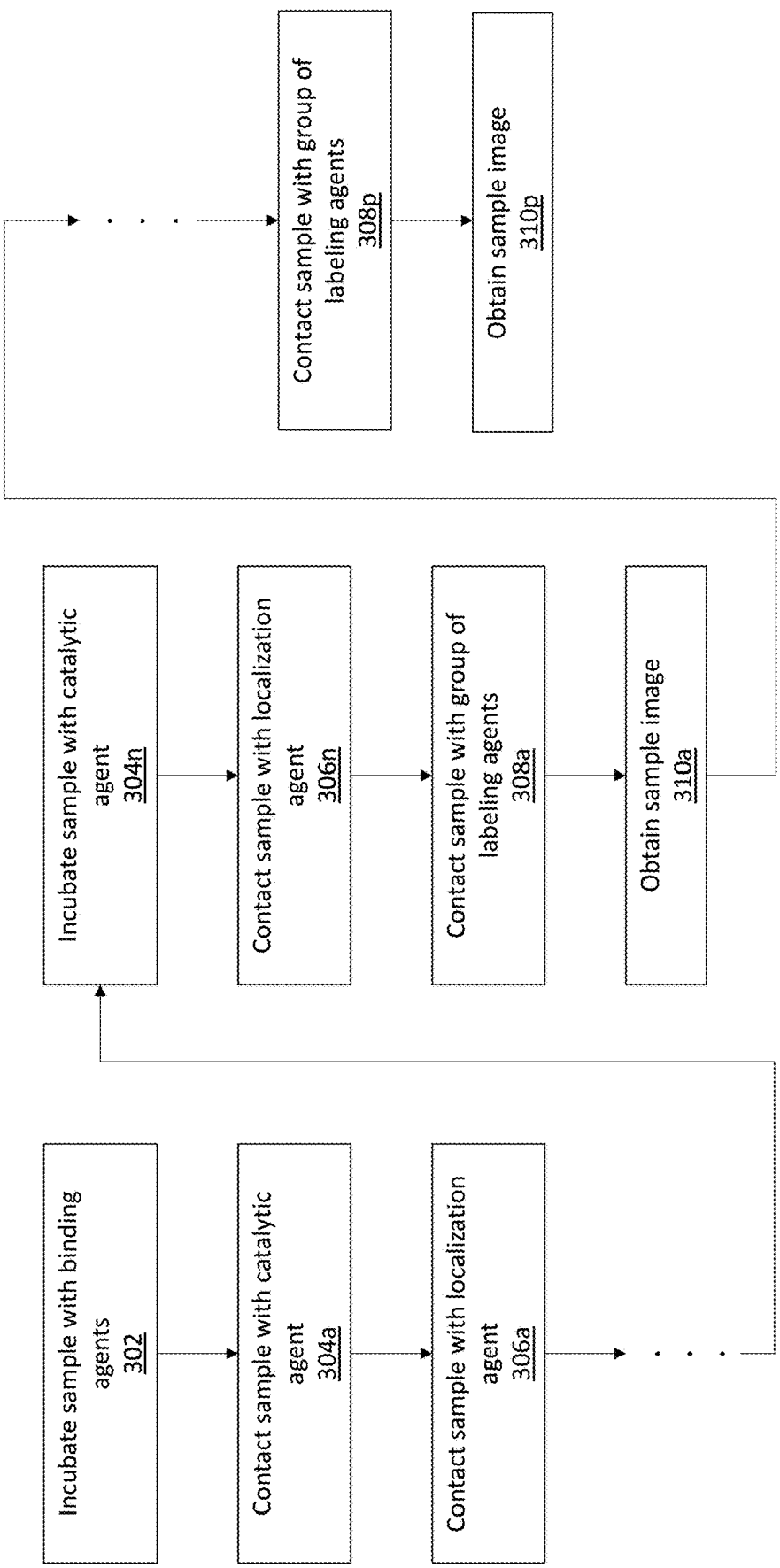
FIG. 3 is a flow chart showing a set of example steps for labeling and imaging a sample to detect multiple different analytes.

FIG. 3 is a flow chart showing a series of example steps corresponding to one implementation of the methods described herein for detecting analytes in a sample. In a first step 302, the sample is incubated with a plurality of different types of binding agents. Each different type of binding agent includes a binding moiety specific to a particular target analyte, and a first nucleotide having a sequence that is associated with the binding moiety.

Next, in step 304a, the sample is contacted with a catalytic agent that includes an enzyme linked to a second oligonucleotide. The sequence of the second oligonucleotide is complementary to only one of the different first oligonucleotides from step 302, and selectively hybridizes to that first oligonucleotide, localizing the catalytic agent in the sample. Then, in step 306a, the sample is contacted with a localization agent that includes an enzyme substrate linked to a third oligonucleotide. A catalytic reaction between the enzyme and substrate deposits molecules of the localization agent in the vicinity of the particular target analyte in the sample.

Steps 304a and 306a are repeated N times (as steps 304n and 306n, where n=b . . . N) for each of N different target analytes in the sample. Each different type of catalytic agent introduced in steps 304n selectively hybridizes to a different one of the binding agents specific for a different target analyte in the sample. Each different type of localization agent introduced in steps 306n is deposited proximity to target analyte for which the catalytic agent in step 304n is selectively associated, and has a third oligonucleotide sequence that is unique among the sequences of the different types of localization agents.

Next in step 308a, a group of one or more different types of labeling agents—each type of which has a fourth oligonucleotide with a sequence that is complementary to only one of the types of localization agents—contacts the sample. Each different type of labeling agent hybridizes with its complementary localization agent, and has an optical label. In step 310a, an image of the sample is obtained showing contributions from each of the different optical labels of the labeling agents. Due to the localization of the labeling agents by virtue of their hybridization to complementary localization agents, the optical labels of each type of labeling agent indicate the presence of a different one of the target analytes in the sample.

Steps 308a and 310a are repeated P times for P different groups of labeling agents (as steps 308p and 310p, where p=a . . . P). In some embodiments, for example, each group P of labeling agents includes only a single labeling agent. In certain embodiments, each group P of labeling agents includes more than one (e.g., two, three, four, five, six, eight, 10, or even more than 10) labeling agents, each of which are detected in the image that is obtained in step 310p. It should be noted that the number of labeling agents detected in each step 310p can be the same or different.

After all labeling agents have been introduced into the sample and all sample images have been obtained, the procedure shown in FIG. 3 terminates.

Oligonucleotides

An oligonucleotide is a molecule that includes multiple nucleotides (e.g., at least some of which may be connected to form a chain). Oligonucleotides described herein can comprise ribonucleic acids. Oligonucleotides described herein can comprise deoxyribonucleic acids. In some embodiments, oligonucleotides can be any sequence, including a user-specified sequence.

Sometimes, an oligonucleotide can be composed of G, A, T and C, or bases that are capable of base pairing reliably with a complementary nucleotide. 7-deaza-adenine, 7-deaza-guanine, adenine, guanine, cytosine, thymine, uracil, 2-deaza-2-thio-guanosine, 2-thio-7-deaza-guanosine, 2-thio-adenine, 2-thio-7-deaza-adenine, isoguanine, 7-deaza-guanine, 5,6-dihydrouridine, 5,6-dihydrothymine, xanthine, 7-deaza-xanthine, hypoxanthine, 7-deaza-xanthine, 2,6 diamino-7-deaza purine, 5-methyl-cytosine, 5-propynyl-uridine, 5-propynyl-cytidine, 2-thio-thymine or 2-thio-uridine are examples of such bases, although many others are known. An oligonucleotide may be an LNA, a PNA, a UNA, or an morpholino oligomer, for example. The oligonucleotides used herein may contain natural or non-natural nucleotides or linkages.

Herein, an antibody, antibody fragment, or another analyte-targeting moiety can be conjugated to a first oligonucleotide to form a binding agent, such that at least a portion of the antibody, antibody fragment, or other analyte-targeting moiety can contact an analyte of the biological sample. The first oligonucleotide can then hybridize to a binding region of a second oligonucleotide, wherein the second oligonucleotide is conjugated to an enzyme capable of mediating the deposition of a another molecule on the biological sample.

In some embodiments, the first oligonucleotide comprises a plurality of ribonucleic acids. In some embodiments, the first oligonucleotide comprises a plurality of deoxyribonucleic acids. In some embodiments, the first oligonucleotide can comprise one or more synthetic nucleotides.

Examples of synthetic nucleotides may include RNA analogues or DNA analogues. Some synthetic nucleotides can comprise artificial nucleic acids, which may comprise peptide nucleic acid, morpholino and locked nucleic acid, glycol nucleic acid, or threose nucleic acid.

The first oligonucleotide can have a given length appropriate for a particular workflow. In some embodiments, a longer oligonucleotide may be selected. In some embodiments, a shorter oligonucleotide may be selected. Factors which affect the selection of oligonucleotide length can include, for example, melting temperature, secondary structure, affinity, specificity, selectivity, cost, and/or combinatorial number of possible sequences.

In some embodiments, the first oligonucleotide can be at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 nucleotides long.

In some embodiments, the first oligonucleotide can be between 5-30, 5-25, 5-20, 10-20, 10-30, between 10-50, between 10-70, between 10-100, between 20-50, between 20-70, between 20-100, between 30-50, between 30-70, between 30-100, between 40-70, between 40-100, between 50-70, between 50-100, between 60-70, between 60-80, between 60-90, or between 60-100 nucleotides in length.

In some embodiments, the first oligonucleotide can be no more than 5, no more than 10, no more than 15, no more than 20, no more than 25, no more than 30, no more than 35, no more than 40, no more than 45, no more than 50, no more than 55, no more than 60, no more than 65, no more than 70, no more than 75, no more than 80, no more than 85, no more than 90, no more than 95, or no more than 100 nucleotides long.

In some embodiments, the first oligonucleotide can be wholly single stranded. In some embodiments, the first oligonucleotide can be partially double stranded. In some embodiments, the partially double stranded region can be at the 3' end of the nucleotide, at the 5' end of the nucleotide, or between the 5' end and 3' end of the nucleotide. In some embodiments, there may be more than one double stranded region. Some first oligonucleotides may have a secondary structure. Some first oligonucleotides may have a secondary structure such that the folding of a single strand and/or its complementarity to itself can produce one or more double stranded regions comprising a single strand.

A second oligonucleotide, conjugated to an enzyme to form a catalytic agent, can hybridize to the first oligonucleotide at a binding region of the second oligonucleotide. This interaction can occur via base pairing.

The binding region of the second oligonucleotide can be at least partially complementary to at least a portion of the first oligonucleotide. In some embodiments, the binding region can be complementary to the 3' end of the first oligonucleotide. In some embodiments, the first binding region can be complementary to the 5' end of the first oligonucleotide. In some embodiments, the first binding region can be complementary to a region between the 3' end and 5' end of the first oligonucleotide. In some embodiments, the binding region can be complementary to the entire first oligonucleotide. In some embodiments, the binding region can be complementary to less than 100% of the first oligonucleotide, as discussed previously.

In some embodiments, the second oligonucleotide can be at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 nucleotides long.

In some embodiments, the second oligonucleotide can be between 5-30, between 5-25, between 5-20, between 10-20, between 10-30, between 10-50, between 10-70, between 10-100, between 20-50, between 20-70, between 20-100, between 30-50, between 30-70, between 30-100, between 40-70, between 40-100, between 50-70, between 50-100, between 60-70, between 60-80, between 60-90, or between 60-100 nucleotides in length.

In some embodiments, the second oligonucleotide can be no more than 5, no more than 10, no more than 15, no more than 20, no more than 25, no more than 30, no more than 35, no more than 40, no more than 45, no more than 50, no more than 55, no more than 60, no more than 65, no more than 70, no more than 75, no more than 80, no more than 85, no more than 90, no more than 95, or no more than 100 nucleotides long.

In some embodiments, the second oligonucleotide can be wholly single stranded. In some embodiments, the first oligonucleotide can be partially double stranded. In some embodiments, the partially double stranded region can be at the 3' end of the nucleotide, at the 5' end of the nucleotide, or between the 5' end and 3' end of the nucleotide. In some embodiments, there may be more than one double stranded region. Some second oligonucleotides may have a secondary structure. Some second oligonucleotides may have a secondary structure such that the folding of a single strand and/or its complementarity to itself can produce one or more double stranded regions comprising a single strand. In some embodiments, a second oligonucleotide can comprise more than one oligonucleotide.

A third oligonucleotide with sequence $S_k$ is conjugated to an enzyme substrate to form a localization agent suitable for TSA amplification, such as a tyramide compound, p-hydroxycinnamic acid, or derivatives of these as discussed previously. The conjugation can be indirect, for example via an additional linker oligonucleotide, via a secondary antibody or nanobody, or any of the other mechanisms discussed previously.

A fourth oligonucleotide with sequence $S_k'$ is conjugated to an optical label to form a labeling agent. The conjugation can be indirect, for example via an additional linker oligonucleotide, or by other mechanism. Typically the optical label is a dye molecule, and can be a fluorescent moiety, a chromogenic moiety, or more generally, any other type of moiety that generates a detectable signal when exposed to illumination light.

The optical label can be a fluorescent dye molecule or moiety such as Alexa Fluor® 488, Alexa Fluor® 514, Alexa Fluor® 568, Alexa 5117 Alexa Fluor® 546, Alexa Fluor® 750, Cy3, Cy3.5, Cy5, Cy5.5, Cy7, fluorescein, rhodamine, tetramethyl rhodamine, Texas Red®, coumarin, DyLight® dyes, Atto® dyes, dilithium 5-carboxy-2-(3,6-diamino-4,5-disulfonato-9-xantheniumyl)benzoate, dilithium 4-carboxy-2-(3,6-diamino-4,5-disulfonato-9-xantheniumyl)benzoate, 6-(2-carboxy-4-{[(2,5-dioxo-1-pyrrolidinyl)oxy]carbonyl}phenyl)-9-iminio-2,2,4-trimethyl-12-sulfo-1,3,4,9-tetrahydro-2H-chromeno [3,2-g] quinoline-10-sulfonate, 6-(2-carboxy-5-{[(2,5-dioxo-1-pyrrolidinyl)oxy]carbonyl}phenyl)-9-iminio-2,2,4-trimethyl-12-sulfo-1,3,4,9-tetrahydro-2H-chromeno [3,2-g] quinoline-10-sulfonate, [6-(2-carboxy-5-{[(2,5-dioxo-1-pyrrolidinyl)oxy]carbonyl}phenyl)-2,2,10,10-tetramethyl-8-(sulfomethyl)-10,11-dihydro-2H-pyrido[3',2':6,7]chromeno[3,2-g]quinolin-1-ium-4-yl]methanesulfonate, sodium hydrogen 6-(2-carboxy-3,4,6-trichloro-5-{124 {6-[(2,5-dioxo-1-pyrrolidinyl)oxy]-6-oxohexyl}amino)-2-oxoethyl]sulfanyl}phenyl)-2,2,4,8,10,10-hexamethyl-1,3,4,8,9,10-hexahydro-2H-pyrido[3',2':6,7]chromeno[3,2-g]quinoline-12,14-disulfonate (1:1:1), 5-(chlorosulfonyl)-2-(2,3,6,7,12,13,16,17-octahydro-1H,5H,11H,15H-pyrido[3,2,1-ij] quinolizino[1',9': 6,7,8] chromeno[2,3-f] quinolin-4-ium-9-yl)benzenesulfonate, or others. In some embodiments, the dye molecule or moiety can include one or more quantum dots. In certain embodiments, the dye molecule or moiety can include one or more chromogenic species.

The fourth oligonucleotide can hybridize to the third oligonucleotide at a binding region of the fourth oligonucleotide. This interaction can occur via base pairing.

The binding region of the fourth oligonucleotide can be complementary to at least a portion of the third oligonucleotide. In some embodiments, the binding region can be complementary to the 3' end of the third oligonucleotide. In some embodiments, the binding region can be complementary to the 5' end of the third oligonucleotide. In some embodiments, the binding region can be complementary to a region between the 3' end and 5' end of the third oligonucleotide. In some embodiments, the binding region can be complementary to the entire third oligonucleotide. In some embodiments, the binding region can be complementary to less than 100% of the third oligonucleotide.

In the methods described herein, the sample is contacted with one or more binding agents that include a binding moiety conjugated to an oligonucleotide having a first oligonucleotide with sequence $S_i$. As discussed above, suitable binding moieties include antibodies, antibody fragments, and other moieties that selectively bind to proteins, markers, peptides, peptide fragments, and other amino acid-containing species that are target analytes in the sample. Methods for preparing suitable binding agents by conjugating binding moieties to oligonucleotides are described, for example, in U.S. Pat. No. 5,391,723, and in Dennler et al., Antibodies 4: 197-224 (2015) and Kozlov et al., Biopolymers 73:621 (2004), the entire contents of each of which are incorporated by reference herein.

The sample is also contacted with one or more catalytic agents that include an enzyme linked to a second oligonucleotide with sequence $S_i'$. Methods for preparing suitable catalytic agents by linking enzymes to oligonucleotides are described, for example, in van Gijlswijk et al., Cytogenet. Cell Genet. 75: 258-262 (1996), the entire contents of which are incorporated by reference herein.

The sample is further contacted with one or more localization agents which include an enzyme substrate linked to a third oligonucleotide having sequence $S_k$. Methods for preparing suitable localization agents by linking enzyme substrates to oligonucleotides are described, for example, in Spicer et al., Chem. Rev. 118(16): 7702-7743 (2018), in Winkler, Ther. Deliv. 4(7): 791-809 (2013), and in van Gijlswijk et al., Histochemie 113(3): 175-180 (2000), the entire contents of each of which are incorporated by reference herein.

The sample is also contacted with one or more localization agents which include an optical label (e.g., a fluorescent or chromogenic moiety) linked to an oligonucleotide of sequence $S_k'$. Methods for preparing suitable labeling agents are described, for example, in Wood et al., "Fluorescence Labeling of Nucleic Acids," Encylcopedia of Biophysics (2013), in Hwang, Molecules 23(1): 124 (2018), and in Taskova et al., Bioconjugate Chem. 30(12): 3007-3012 (2019), the entire contents of each of which are incorporated by reference herein.

Process Reagents and Conditions

The antibody, antibody fragment, or other analyte-targeting moiety conjugated to the first oligonucleotide (the binding agent) can be delivered to the sample in a first buffer. The first buffer can comprise PBS, PBS-T, TBS, TBS-T water, saline, or Kreb's buffer and can include blocking material. In some embodiments, blocking material can comprise BSA, casein, sheared salmon-sperm DNA, other oligonucleotide components, rat IgG and/or mouse IgG.

The oligonucleotide-conjugated enzyme molecules (the catalytic agent) can be delivered to the sample in a second buffer. In some embodiments, the second buffer can comprise PBS, PBS-T, TBS, TB S-T water, saline, or Kreb's buffer.

The oligonucleotide-conjguated enzyme substrate (the localization agent) and the oligonucleotide-conjugated dye molecules (the labeling agent) can be delivered to the sample in the first or second buffers.

In some embodiments, the first buffer can be essentially the same as the second buffer.

In some embodiments, the antibody conjugated to the first oligonucleotide can be in the same buffer as the second oligonucleotide, which can be a first alternate buffer. In some embodiments, the first alternate buffer can comprise PBS, PBS-T, TBS, TB S-T water, saline, or Kreb's buffer.

In some embodiments, the sample is subjected to buffers that promote hybridization and can include DNA components, protein components, chaotropic reagents at concentrations of 5%, 10%, 15% or 20%, and detergent solutions.

In some embodiments, the sample is subjected to buffers that promote dehybridization and can include chaotropic reagents such as DMSO and formamide at concentrations of 60%, 70%, 80% or 90%.

The oligonucleotide-linked enzyme molecules (e.g., the catalytic agent) can be removed from the sample, for example through dehybridization between the oligonucleotides conjugated directly or indirectly to the enzyme and antibody components. In some embodiments, this dehybridization can be performed using chaotropic reagents, for example DMSO or formamide. The dehybridization step can therefore remove directed enzymatic activity from the sample surface, which can enable subsequent rounds of hybridization and enzyme-catalyzed oligonucleotide deposition without signal contamination from non-targeted moieties.

The oligonucleotide-linked dye molecules (e.g., the labeling agent) can be removed from the sample surface, for example through dehybridization between the oligonucleotides conjugated directly or indirectly to the dye and TSA-deposited oligonucleotide components. In some embodiments, this dehybridization can be performed using chaotropic reagents, for example DMSO or formamide. The dehybridization step can therefore remove dye from the sample surface, which can enable subsequent rounds of detection without signal contamination from this round of dyes.

In some preferred embodiments of this type, at least some of the primary antibodies can be used to identify cell type or identity, and at least some of primary antibodies indicate cellular activity, expression or signaling state.

Compositions and Kits

Any of the reagents, molecules, and other substances described herein can be combined to form compositions that are delivered to biological samples for the purpose of performing one or more steps of the various methods described. Reagents, molecules, and other substances described in any of the documents incorporated by reference can also be present in the compositions.

Kits that include any of the compositions can also include instructions for performing any of the method steps described herein. Such kits can include a housing or packaging formed of one or more materials such as paper, metals, and plastics. The housing can be implemented in a variety of forms, including as one or more tubular containers such as vials, blister packages, and other sealed containers. The instructions can be positioned within, attached to, or accompany the kit housing.

Imaging Systems and Methods

A wide variety of different imaging systems can be used to obtain the images described herein. Certain commercial systems, such as the Vectra Polaris system (available from Akoya Biosciences, Inc.) can be used. Aspects of the imaging systems that can be used are described, for example, in U.S. Patents 7,155,55, 7,019,777, 9,107,624, and in PCT Patent Application Publication No. WO 2005/040769, the entire contents of each of which are incorporated herein by reference.

To obtain the images of the sample described herein, the sample is exposed to illumination light from a light source of the imaging system. A detector of the imaging system (e.g., an imaging detector such as a CCD array) is used to obtain an image of the sample by detecting light emitted from the sample in response to the illumination light. The emitted light can be fluorescence emission, illumination light transmitted through the sample, illumination light reflected from the sample, or a combination of any of these. Individual elements of the detector measure the emitted light, forming a two-dimensional image of the biological sample. Because the emitted light corresponds to locations in the sample where labeling agents are located, locations of the analytes are indicated by the optical labels of the labeling agents.

Similar methods are used to obtain images of counterstains applied to samples as described herein. As counterstains bind non-specifically to sample structures, counterstain images typically do not indicate locations of specific analytes, but instead provide more general information about sample structures, features, and morphology.

EXAMPLES

To evaluate the methods described above, a 5 micron thick tissue section was excised from a formalin-fixed, paraffin-embedded human tonsil block. The section was deparaffined, hydrated, and subjected to antigen retrieval with a citrate buffer. The sample was then stained with a CD20 (L20) antibody obtained from Akoya Biosciences, Inc. (Menlo Park, CA), following staining instructions that accompanied the antibody. The CD20 antibody used for staining was pre-conjugated to an oligonucleotide (sequence BX015, obtained from Akoya Biosciences, Inc.) according to the manufacturer's instructions.

Following staining, the tissue section was fixed in paraformaldehyde, ice-cold methanol, and a CODEX® fixative reagent (obtained from Akoya Biosciences, Inc.), and then washed. The tissue section was equilibrated with 20% dimethylsulfoxide (DMSO) in 1× CODEX® assay buffer (obtained from Akoya Biosciences, Inc.) for 10 minutes.

After equilibration, the tissue section was hybridized with 5 μL of a 2011M solution of a horseradish peroxidase (HRP)-conjugated oligonucleotide. The HRP-conjugated oligonucleotide had a nucleotide sequence complementary to the BX015 sequence. Following hybridization, the tissue section was washed three times with CODEX® assay buffer.

A reagent consisting of a DNA oligonucleotide having a sequence BX006 (obtained from Akoya Biosciences, Inc.) was conjugated with a tyramine moiety at the C10 carboxy linker at the 5' end of the sequence. The tissue sample was then contacted with the reagent in 1× CODEX® buffer and allowed to react for 10 minutes.

Following the reaction, the HRP-conjugated oligonucleotide was dehybridized from the tissue section according to the CODEX® clear tissue protocol described in the CODEX® user manual available from Akoya Biosciences, Inc., for example at internet address www.akoyabio.com/support/reagents/.

In preparation for imaging, the tissue section was incubated with a CODEX® reporter reagent Cy5-RX006 (available from Akoya Biosciences, Inc.) in CODEX® hybridization buffer. The tissue section was imaged using a Keyence microscope.

Figure 4:
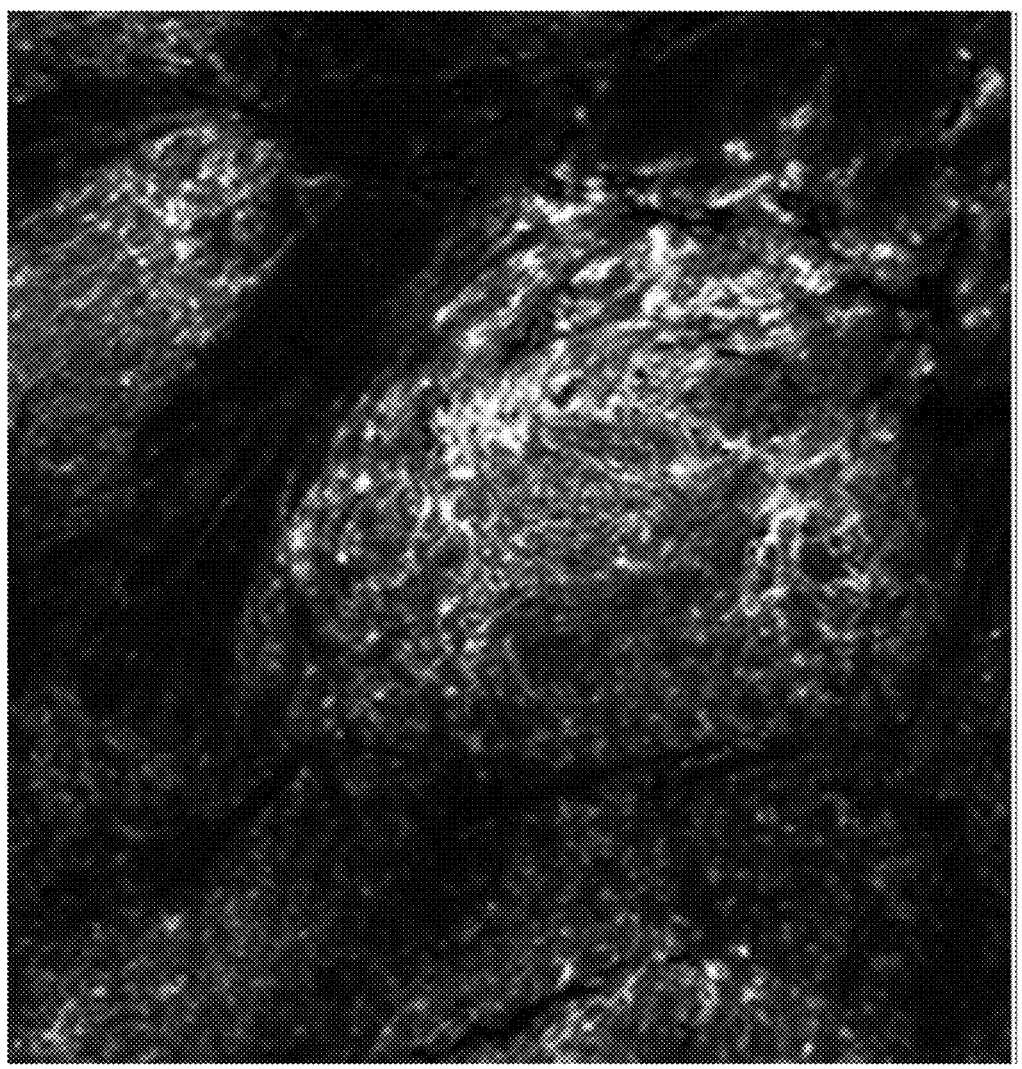
FIG. 4 is an image of a tissue section stained with an oligonucleotide-linked CD20 antibody and labeled with labeling agent localized in the vicinity of the CD20 antibody.

FIG. 4 shows an image of the tissue section. Within the tissue section, brighter regions correspond to CD20-localized tyramine-conjugated oligonucleotide sequence (i.e., the BX006 sequence).

Figure 5:
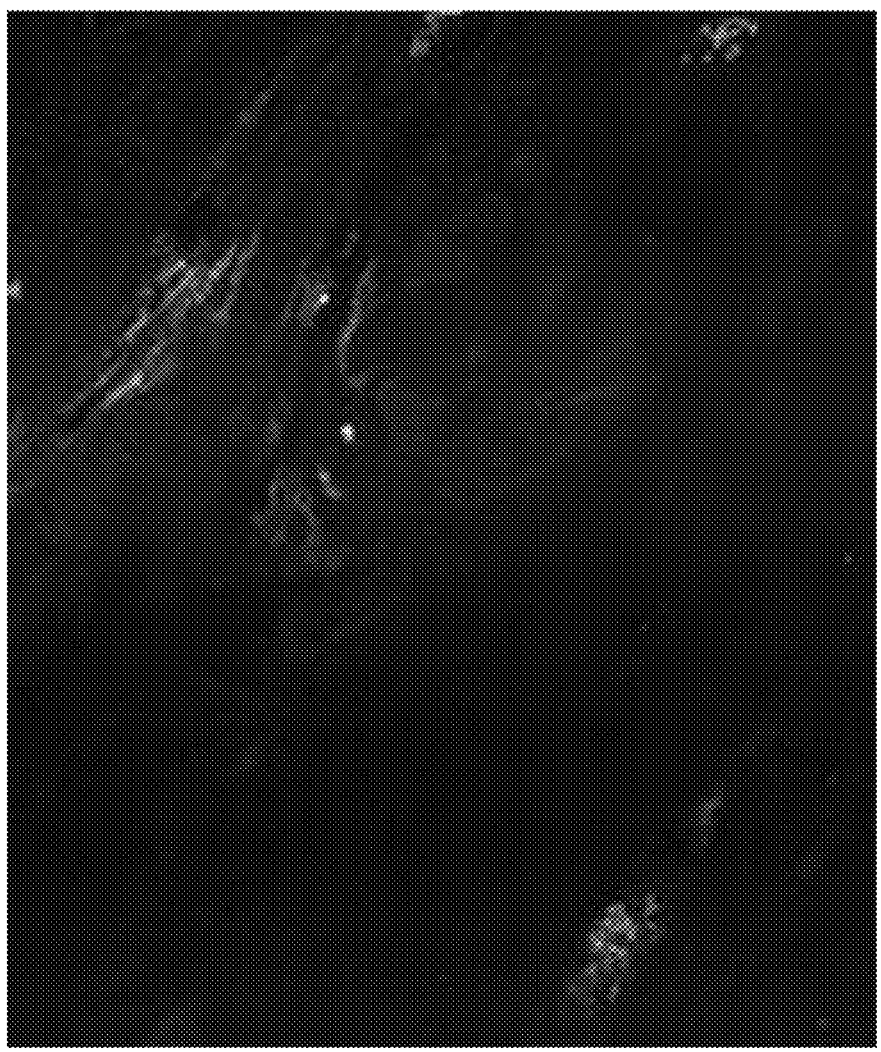
FIG. 5 is an image of the tissue section of FIG. 4 after removal of the labeling agent.

After imaging, the reporter reagent was dehybridized from the tissue section using the CODEX® clear tissue protocol. Another image of the tissue section with the reporter reagent removed is shown in FIG. 5. This image illustrates an absence of signal intensity corresponding to the CD20-localized tyramine-conjugated oligonucleotide sequence, suggesting near-complete removal of the reporter reagent during dehybridization.

OTHER EMBODIMENTS

While certain embodiments of the present disclosure have been shown and described herein, it will be obvious to those skilled in the art that such embodiments are provided by way of example only. Numerous variations, changes, and substitutions will be apparent to those skilled in the art. It should be understood that various alternatives to the embodiments specifically described herein are within the scope of this disclosure.

What is claimed is:

1. A method for imaging an analyte in a biological sample, the method comprising:

contacting the biological sample with a binding agent, wherein the binding agent comprises a binding moiety that binds to the analyte and a first oligonucleotide sequence;

contacting the biological sample with a catalytic agent, wherein the catalytic agent comprises a second oligonucleotide sequence linked to an enzyme, and wherein the second oligonucleotide sequence hybridizes to the first oligonucleotide sequence;

contacting the biological sample with a localization agent, wherein the localization agent comprises a substrate complementary to the enzyme and a third oligonucleotide sequence linked to the substrate;

contacting the biological sample with a labeling agent, wherein the labeling agent comprises a fourth oligonucleotide sequence linked to an optical label, wherein the fourth oligonucleotide sequence hybridizes to the third oligonucleotide sequence; and exposing the biological sample to illumination light, detecting emitted light from the biological sample, and forming an image of the biological sample in which a location of the analyte is indicated by the optical label.

2. The method of claim 1, wherein the binding moiety comprises an antibody, an antibody fragment, or an antibody analog.

3. The method of claim 1, wherein the enzyme comprises horseradish peroxidase or a derivative thereof.

4. The method of claim 1, wherein the enzyme comprises a compound that mimics horseradish peroxidase.

5. The method of claim 4, wherein the compound comprises a hemin-containing complex.

6. The method of claim 1, wherein the enzyme comprises soybean peroxidase.

7. The method of claim 1, wherein the third and fourth oligonucleotide sequences comprise different numbers of nucleotides.

8. The method of claim 1, wherein the optical label comprises a fluorescent species.

9. The method of claim 1, wherein the optical label comprises a chromogenic stain.

10. The method of claim 1, wherein the biological sample is a tissue sample.

11. The method of claim 1, wherein the analyte comprises a member selected from the group consisting of a protein, a peptide, and a peptide fragment.

12. The method of claim 1, further comprising, prior to exposing the biological sample to illumination light:
contacting the biological sample with a counterstain; and
exposing the biological sample to illumination light, detecting emitted light from the biological sample, and forming a second image of the sample that shows the location of the counterstain in the biological sample.

13. The method of claim 1, wherein a ratio of an amount of the fourth oligonucleotide sequence to an amount of the first oligonucleotide sequence in the biological sample is greater than 1.

14. The method of claim 1, wherein the binding agent is a first binding agent, the catalytic agent is a first catalytic agent, the localization agent is a first localization agent, the labeling agent is a first labeling agent, the analyte is a first analyte, and the binding moiety is a first binding moiety, the method further comprising contacting the biological sample with a second binding agent, wherein the second binding agent comprises a second binding moiety that binds to a second analyte in the biological sample and a fifth oligonucleotide sequence.

15. The method of claim 14, wherein the second analyte is different from the first analyte.

16. The method of claim 14, wherein the catalytic agent is a first catalytic agent, the enzyme is a first enzyme, the localization agent is a first localization agent, the substrate is a first substrate, the labeling agent is a first labeling agent, and the optical label is a first optical label, the method further comprising:
contacting the biological sample with a second catalytic agent, wherein the second catalytic agent comprises a sixth oligonucleotide sequence linked to a second enzyme, and wherein the sixth oligonucleotide sequence hybridizes to the fifth oligonucleotide sequence;
contacting the biological sample with a second binding agent, wherein the second binding agent comprises a second substrate complementary to the second enzyme and a seventh oligonucleotide sequence linked to the second substrate; and
contacting the biological sample with a second labeling agent, wherein the second labeling agent comprises an eighth oligonucleotide sequence linked to a second optical label, wherein the eighth oligonucleotide sequence hybridizes to the seventh oligonucleotide sequence.

17. The method of claim 16, wherein the first and second optical labels are different.

18. The method of claim 16, wherein the first and second enzymes are different.

19. The method of claim 16, wherein the second enzyme comprises a member selected from the group consisting of horseradish peroxidase, a derivative of horseradish peroxidase, a compound that mimics horseradish peroxidase, a hemin-containing complex, hematin, and soybean peroxidase.

20. The method of claim 16, wherein a ratio of an amount of the eighth oligonucleotide sequence to an amount of the fifth oligonucleotide sequence in the biological sample is different from a ratio of the amount of the fourth oligonucleotide sequence to an amount of the first oligonucleotide sequence in the biological sample.

21. The method of claim 20, wherein the ratio of the amount of the eighth oligonucleotide sequence to the amount of the fifth oligonucleotide sequence in the biological sample is not greater than 1.

22. The method of claim 20, wherein the ratio of the amount of the eighth oligonucleotide sequence to the amount of the fifth oligonucleotide sequence in the biological sample is greater than 1, and the ratio of the amount of the fourth oligonucleotide sequence to the amount of the first oligonucleotide sequence in the biological sample is greater than 1.

23. The method of claim 16, further comprising, prior to contacting the biological sample with the second labeling agent, removing the first labeling agent from the biological sample.

24. The method of claim 23, comprising removing the first labeling agent from the biological sample prior to contacting the biological sample with the second localization agent.

25. The method of claim 23, comprising removing the first labeling agent from the biological sample prior to contacting the biological sample with the second catalytic agent.

26. The method of claim 23, comprising removing the first labeling agent from the biological sample prior to contacting the biological sample with the second binding agent.

27. The method of claim 16, wherein the image of the biological sample is a first image, the method further comprising exposing the biological sample to illumination light, detecting emitted light from the biological sample, and forming a second image of the biological sample in which a location of the second analyte is indicated by the second optical label.

28. The method of claim 27, wherein the first optical label is present in the biological sample when the biological sample is exposed to the illumination light to form the second image of the biological sample.

29. The method of claim 27, further comprising removing the first optical label from the biological sample prior to exposing the biological sample to the illumination light to form the second image of the biological sample.

30. The method of claim 14, wherein the second binding moiety comprises an antibody, an antibody fragment, or an antibody analog.

31. The method of claim 1, further comprising, after contacting the biological sample with the localization agent and prior to contacting the biological sample with the labeling agent:
  contacting the biological sample with a second catalytic agent, wherein the second catalytic agent comprises a fifth oligonucleotide sequence linked to a second enzyme, and wherein the fifth oligonucleotide sequence hybridizes to the third oligonucleotide sequence; and
  contacting the biological sample with a second localization agent, wherein the second localization agent comprises a second substrate complementary to the second enzyme and a sixth oligonucleotide sequence linked to the second substrate,
  wherein the fourth oligonucleotide sequence of the labeling agent hybridizes to the sixth oligonucleotide sequence.

32. A method for imaging an analyte in a biological sample, the method comprising:
  linking an enzyme to the analyte so that the enzyme is localized in the biological sample at a location of the analyte;
  contacting the biological sample with a localization agent comprising a substrate complementary to the enzyme and a first oligonucleotide sequence to deposit the first oligonucleotide sequence in the biological sample adjacent to the location of the analyte;
  contacting the biological sample with a labeling agent comprising a second oligonucleotide sequence that hybridizes to the first oligonucleotide sequence, and an optical label; and
  obtaining an image of the biological sample in which the location of the analyte is represented by a location of the optical label.

* * * * *